(12) United States Patent
Kiani et al.

(10) Patent No.: US 10,855,023 B2
(45) Date of Patent: Dec. 1, 2020

(54) MAGNETIC CONNECTOR FOR A DATA COMMUNICATIONS CABLE

(71) Applicant: MASIMO CORPORATION, Irvine, CA (US)

(72) Inventors: Massi Joe E. Kiani, Laguna Niguel, CA (US); Marcelo M. Lamego, Cupertino, CA (US); Cristiano Dalvi, Lake Forest, CA (US); Hung Vo, Fountain Valley, CA (US)

(73) Assignee: Masimo Corporation, Irvine, CA (US)

( * ) Notice: Subject to any disclaimer, the term of this patent is extended or adjusted under 35 U.S.C. 154(b) by 0 days.

(21) Appl. No.: 16/230,063

(22) Filed: Dec. 21, 2018

(65) Prior Publication Data

US 2019/0221966 A1    Jul. 18, 2019

Related U.S. Application Data

(63) Continuation of application No. 15/288,987, filed on Oct. 7, 2016, now Pat. No. 10,205,272, which is a
(Continued)

(51) Int. Cl.
*H01R 13/62*   (2006.01)
*H01R 11/30*   (2006.01)
*H01R 13/703*  (2006.01)
*A61B 5/0205*  (2006.01)
*A61B 5/145*   (2006.01)
(Continued)

(52) U.S. Cl.
CPC ..... *H01R 13/6205* (2013.01); *A61B 5/02055* (2013.01); *A61B 5/14546* (2013.01); *A61B 5/14551* (2013.01); *A61B 5/6826* (2013.01); *H01R 11/30* (2013.01); *H01R 13/6591* (2013.01); *H01R 13/7037* (2013.01); *H01R 13/631* (2013.01); *H01R 13/7175* (2013.01); *H01R 2201/12* (2013.01); *Y10S 439/95* (2013.01); *Y10T 29/49117* (2015.01)

(58) Field of Classification Search
CPC .. H01R 13/6205; H01R 13/631; Y10S 439/95
See application file for complete search history.

(56) References Cited

U.S. PATENT DOCUMENTS 4,317,969 A * 3/1982 Riegler ............. H01R 13/6205
                                                    200/52 R
4,960,128 A   10/1990 Gordon et al.
(Continued)

*Primary Examiner* — Tho D Ta
(74) *Attorney, Agent, or Firm* — Knobbe Martens Olson & Bear LLP

(57) ABSTRACT

A magnetic connector has a plug core disposed around a plug contact set and a receptacle core disposed around a receptacle contact set. The plug core defines a generally elongated circular plug core edge. The receptacle core defines a generally elongated concentric-circular receptacle core edge. The receptacle core edge defines an air gap and the plug core defines an anchor configured to insert into the air gap. A coil is disposed around the receptacle core, and the coil, the plug core and the air gap define a magnetic circuit. The coil is electrically energized so as to form a magnetic field within an air gap, lock the anchor within the air gap and lock the plug contact set to the receptacle contact set accordingly.

7 Claims, 17 Drawing Sheets

Related U.S. Application Data continuation of application No. 13/783,424, filed on Mar. 4, 2013, now Pat. No. 9,466,919, which is a continuation of application No. 12/721,199, filed on Mar. 10, 2010, now Pat. No. 8,388,353.

(60) Provisional application No. 61/159,336, filed on Mar. 11, 2009.

(51) Int. Cl.
  *A61B 5/1455* (2006.01)
  *A61B 5/00* (2006.01)
  *H01R 13/6591* (2011.01)
  *H01R 13/717* (2006.01)
  *H01R 13/631* (2006.01)

(56) References Cited

U.S. PATENT DOCUMENTS

| | | |
|---|---|---|
| 4,964,408 A | 10/1990 | Hink et al. |
| 5,041,187 A | 8/1991 | Hink et al. |
| 5,069,213 A | 12/1991 | Polczynski |
| 5,163,438 A | 11/1992 | Gordon et al. |
| 5,319,355 A | 6/1994 | Russek |
| 5,337,744 A | 8/1994 | Branigan |
| 5,341,805 A | 8/1994 | Stavridi et al. |
| 5,342,204 A * | 8/1994 | Och ................ F21V 21/08 439/39 |
| D353,195 S | 12/1994 | Savage et al. |
| D353,196 S | 12/1994 | Savage et al. |
| 5,377,676 A | 1/1995 | Vari et al. |
| D359,546 S | 6/1995 | Savage et al. |
| 5,431,170 A | 7/1995 | Mathews |
| D361,840 S | 8/1995 | Savage et al. |
| D362,063 S | 9/1995 | Savage et al. |
| 5,452,717 A | 9/1995 | Branigan et al. |
| D363,120 S | 10/1995 | Savage et al. |
| 5,456,252 A | 10/1995 | Vari et al. |
| 5,479,934 A | 1/1996 | Imran |
| 5,482,036 A | 1/1996 | Diab et al. |
| 5,490,505 A | 2/1996 | Diab et al. |
| 5,494,043 A | 2/1996 | O'Sullivan et al. |
| 5,533,511 A | 7/1996 | Kaspari et al. |
| 5,534,851 A | 7/1996 | Russek |
| 5,561,275 A | 10/1996 | Savage et al. |
| 5,562,002 A | 10/1996 | Lalin |
| 5,568,815 A | 10/1996 | Raynes et al. |
| 5,590,649 A | 1/1997 | Caro et al. |
| 5,602,924 A | 2/1997 | Durand et al. |
| 5,632,272 A | 5/1997 | Diab et al. |
| 5,638,816 A | 6/1997 | Kiani-Azarbayjany et al. |
| 5,638,818 A | 6/1997 | Diab et al. |
| 5,645,440 A | 7/1997 | Tobler et al. |
| 5,685,299 A | 11/1997 | Diab et al. |
| D393,830 S | 4/1998 | Tobler et al. |
| 5,743,262 A | 4/1998 | Lepper, Jr. et al. |
| 5,758,644 A | 6/1998 | Diab et al. |
| 5,760,910 A | 6/1998 | Lepper, Jr. et al. |
| 5,769,785 A | 6/1998 | Diab et al. |
| 5,782,757 A | 7/1998 | Diab et al. |
| 5,785,659 A | 7/1998 | Caro et al. |
| 5,791,347 A | 8/1998 | Flaherty et al. |
| 5,810,734 A | 9/1998 | Caro et al. |
| 5,823,950 A | 10/1998 | Diab et al. |
| 5,830,131 A | 11/1998 | Caro et al. |
| 5,833,618 A | 11/1998 | Caro et al. |
| 5,860,919 A | 1/1999 | Kiani-Azarbayjany et al. |
| 5,890,929 A | 4/1999 | Mills et al. |
| 5,904,654 A | 5/1999 | Wohltmann et al. |
| 5,919,134 A | 7/1999 | Diab |
| 5,934,925 A | 8/1999 | Tobler et al. |
| 5,940,182 A | 8/1999 | Lepper, Jr. et al. |
| 5,987,343 A | 11/1999 | Kinast |
| 5,995,855 A | 11/1999 | Kiani et al. |
| 5,997,343 A | 12/1999 | Mills et al. |
| 6,002,952 A | 12/1999 | Diab et al. |
| 6,011,986 A | 1/2000 | Diab et al. |
| 6,027,452 A | 2/2000 | Flaherty et al. |
| 6,036,642 A | 3/2000 | Diab et al. |
| 6,045,509 A | 4/2000 | Caro et al. |
| 6,067,462 A | 5/2000 | Diab et al. |
| 6,081,735 A | 6/2000 | Diab et al. |
| 6,088,607 A | 7/2000 | Diab et al. |
| 6,110,522 A | 8/2000 | Lepper, Jr. et al. |
| 6,124,597 A | 9/2000 | Shehada |
| 6,128,521 A | 10/2000 | Marro et al. |
| 6,129,675 A | 10/2000 | Jay |
| 6,144,868 A | 11/2000 | Parker |
| 6,151,516 A | 11/2000 | Kiani-Azarbayjany et al. |
| 6,152,754 A | 11/2000 | Gerhardt et al. |
| 6,157,850 A | 12/2000 | Diab et al. |
| 6,165,005 A | 12/2000 | Mills et al. |
| 6,184,521 B1 | 2/2001 | Coffin, IV et al. |
| 6,206,830 B1 | 3/2001 | Diab et al. |
| 6,229,856 B1 | 5/2001 | Diab et al. |
| 6,232,609 B1 | 5/2001 | Snyder et al. |
| 6,236,872 B1 | 5/2001 | Diab et al. |
| 6,241,683 B1 | 6/2001 | Macklem et al. |
| 6,253,097 B1 | 6/2001 | Aronow et al. |
| 6,256,523 B1 | 7/2001 | Diab et al. |
| 6,263,222 B1 | 7/2001 | Diab et al. |
| 6,278,522 B1 | 8/2001 | Lepper, Jr. et al. |
| 6,280,213 B1 | 8/2001 | Tobler et al. |
| 6,285,896 B1 | 9/2001 | Tobler et al. |
| 6,301,493 B1 | 10/2001 | Marro et al. |
| 6,308,089 B1 | 10/2001 | von der Ruhr et al. |
| 6,317,627 B1 | 11/2001 | Ennen et al. |
| 6,321,100 B1 | 11/2001 | Parker |
| 6,325,761 B1 | 12/2001 | Jay |
| 6,334,065 B1 | 12/2001 | Al-Ali et al. |
| 6,343,224 B1 | 1/2002 | Parker |
| 6,349,228 B1 | 2/2002 | Kiani et al. |
| 6,360,114 B1 | 3/2002 | Diab et al. |
| 6,368,283 B1 | 4/2002 | Xu et al. |
| 6,371,921 B1 | 4/2002 | Caro et al. |
| 6,377,829 B1 | 4/2002 | Al-Ali |
| 6,388,240 B2 | 5/2002 | Schulz et al. |
| 6,397,091 B2 | 5/2002 | Diab et al. |
| 6,430,437 B1 | 8/2002 | Marro |
| 6,430,525 B1 | 8/2002 | Weber et al. |
| 6,463,311 B1 | 10/2002 | Diab |
| 6,470,199 B1 | 10/2002 | Kopotic et al. |
| 6,501,975 B2 | 12/2002 | Diab et al. |
| 6,505,059 B1 | 1/2003 | Kollias et al. |
| 6,515,273 B2 | 2/2003 | Al-Ali |
| 6,519,487 B1 | 2/2003 | Parker |
| 6,525,386 B1 | 2/2003 | Mills et al. |
| 6,526,300 B1 | 2/2003 | Kiani et al. |
| 6,541,756 B2 | 4/2003 | Schulz et al. |
| 6,542,764 B1 | 4/2003 | Al-Ali et al. |
| 6,580,086 B1 | 6/2003 | Schulz et al. |
| 6,584,336 B1 | 6/2003 | Ali et al. |
| 6,595,316 B2 | 7/2003 | Cybulski et al. |
| 6,597,932 B2 | 7/2003 | Tian et al. |
| 6,597,933 B2 | 7/2003 | Kiani et al. |
| 6,606,511 B1 | 8/2003 | Ali et al. |
| 6,632,181 B2 | 10/2003 | Flaherty et al. |
| 6,639,668 B1 | 10/2003 | Trepagnier |
| 6,640,116 B2 | 10/2003 | Diab |
| 6,643,530 B2 | 11/2003 | Diab et al. |
| 6,650,917 B2 | 11/2003 | Diab et al. |
| 6,654,624 B2 | 11/2003 | Diab et al. |
| 6,658,276 B2 | 12/2003 | Kiani et al. |
| 6,661,161 B1 | 12/2003 | Lanzo et al. |
| 6,670,583 B2 * | 12/2003 | Kara ................ A47J 36/2472 219/432 |
| 6,671,531 B2 | 12/2003 | Al-Ali et al. |
| 6,678,543 B2 | 1/2004 | Diab et al. |
| 6,684,090 B2 | 1/2004 | Ali et al. |
| 6,684,091 B2 | 1/2004 | Parker |
| 6,697,656 B1 | 2/2004 | Al-Ali |
| 6,697,657 B1 | 2/2004 | Shehada et al. |
| 6,697,658 B2 | 2/2004 | Al-Ali |
| RE38,476 E | 3/2004 | Diab et al. |

(56) References Cited

U.S. PATENT DOCUMENTS

| | | |
|---|---|---|
| 6,699,194 B1 | 3/2004 | Diab et al. |
| 6,714,804 B2 | 3/2004 | Al-Ali et al. |
| RE38,492 E | 4/2004 | Diab et al. |
| 6,721,582 B2 | 4/2004 | Trepagnier et al. |
| 6,721,585 B1 | 4/2004 | Parker |
| 6,725,075 B2 | 4/2004 | Al-Ali |
| 6,728,560 B2 | 4/2004 | Kollias et al. |
| 6,735,459 B2 | 5/2004 | Parker |
| 6,745,060 B2 | 6/2004 | Diab et al. |
| 6,760,607 B2 | 7/2004 | Al-Ali |
| 6,770,028 B1 | 8/2004 | Ali et al. |
| 6,771,994 B2 | 8/2004 | Kiani et al. |
| 6,792,300 B1 | 9/2004 | Diab et al. |
| 6,813,511 B2 | 11/2004 | Diab et al. |
| 6,816,741 B2 | 11/2004 | Diab |
| 6,822,564 B2 | 11/2004 | Al-Ali |
| 6,826,419 B2 | 11/2004 | Diab et al. |
| 6,830,711 B2 | 12/2004 | Mills et al. |
| 6,850,787 B2 | 2/2005 | Weber et al. |
| 6,850,788 B2 | 2/2005 | Al-Ali |
| 6,852,083 B2 | 2/2005 | Caro et al. |
| 6,861,639 B2 | 3/2005 | Al-Ali |
| 6,897,370 B2 * | 5/2005 | Kondo ............... H01R 13/6205 |
| | | 136/243 |
| 6,898,452 B2 | 5/2005 | Al-Ali et al. |
| 6,920,345 B2 | 7/2005 | Al-Ali et al. |
| 6,931,268 B1 | 8/2005 | Kiani-Azarbayjany et al. |
| 6,934,570 B2 | 8/2005 | Kiani et al. |
| 6,939,305 B2 | 9/2005 | Flaherty et al. |
| 6,943,348 B1 | 9/2005 | Coffin, IV |
| 6,950,687 B2 | 9/2005 | Al-Ali |
| 6,961,598 B2 | 11/2005 | Diab |
| 6,970,792 B1 | 11/2005 | Diab |
| 6,979,812 B2 | 12/2005 | Al-Ali |
| 6,985,764 B2 | 1/2006 | Mason et al. |
| 6,993,371 B2 | 1/2006 | Kiani et al. |
| 6,996,427 B2 | 2/2006 | Ali et al. |
| 6,999,904 B2 | 2/2006 | Weber et al. |
| 7,003,338 B2 | 2/2006 | Weber et al. |
| 7,003,339 B2 | 2/2006 | Diab et al. |
| 7,015,451 B2 | 3/2006 | Dalke et al. |
| 7,024,233 B2 | 4/2006 | Ali et al. |
| 7,027,849 B2 | 4/2006 | Al-Ali |
| 7,030,749 B2 | 4/2006 | Al-Ali |
| 7,039,449 B2 | 5/2006 | Al-Ali |
| 7,041,060 B2 | 5/2006 | Flaherty et al. |
| 7,044,918 B2 | 5/2006 | Diab |
| 7,048,687 B1 | 5/2006 | Reuss et al. |
| 7,067,893 B2 | 6/2006 | Mills et al. |
| 7,096,052 B2 | 8/2006 | Mason et al. |
| 7,096,054 B2 | 8/2006 | Abdul-Hafiz et al. |
| 7,132,641 B2 | 11/2006 | Schulz et al. |
| 7,142,901 B2 | 11/2006 | Kiani et al. |
| 7,149,561 B2 | 12/2006 | Diab |
| 7,186,966 B2 | 3/2007 | Al-Ali |
| 7,190,261 B2 | 3/2007 | Al-Ali |
| 7,204,695 B1 * | 4/2007 | Shiu ............... H01R 13/6205 |
| | | 439/305 |
| 7,215,984 B2 | 5/2007 | Diab |
| 7,215,986 B2 | 5/2007 | Diab |
| 7,221,971 B2 | 5/2007 | Diab |
| 7,225,006 B2 | 5/2007 | Al-Ali et al. |
| 7,225,007 B2 | 5/2007 | Al-Ali |
| RE39,672 E | 6/2007 | Shehada et al. |
| 7,239,905 B2 | 7/2007 | Kiani-Azarbayjany et al. |
| 7,245,953 B1 | 7/2007 | Parker |
| 7,254,429 B2 | 8/2007 | Schurman et al. |
| 7,254,431 B2 | 8/2007 | Al-Ali |
| 7,254,433 B2 | 8/2007 | Diab et al. |
| 7,254,434 B2 | 8/2007 | Schulz et al. |
| 7,272,425 B2 | 9/2007 | Al-Ali |
| 7,274,955 B2 | 9/2007 | Kiani et al. |
| D554,263 S | 10/2007 | Al-Ali |
| 7,280,858 B2 | 10/2007 | Al-Ali et al. |
| 7,289,835 B2 | 10/2007 | Mansfield et al. |
| 7,292,883 B2 | 11/2007 | De Felice et al. |
| 7,295,866 B2 | 11/2007 | Al-Ali |
| 7,328,053 B1 | 2/2008 | Diab et al. |
| 7,331,793 B2 * | 2/2008 | Hernandez ............... H01F 38/14 |
| | | 439/38 |
| 7,332,784 B2 | 2/2008 | Mills et al. |
| 7,340,287 B2 | 3/2008 | Mason et al. |
| 7,341,559 B2 | 3/2008 | Schulz et al. |
| 7,343,186 B2 | 3/2008 | Lamego et al. |
| D566,282 S | 4/2008 | Al-Ali et al. |
| 7,355,512 B1 | 4/2008 | Al-Ali |
| 7,356,365 B2 | 4/2008 | Schurman |
| 7,371,981 B2 | 5/2008 | Abdul-Hafiz |
| 7,373,193 B2 | 5/2008 | Al-Ali et al. |
| 7,373,194 B2 | 5/2008 | Weber et al. |
| 7,376,453 B1 | 5/2008 | Diab et al. |
| 7,377,794 B2 | 5/2008 | Al Ali et al. |
| 7,377,899 B2 | 5/2008 | Weber et al. |
| 7,383,070 B2 | 6/2008 | Diab et al. |
| 7,415,297 B2 | 8/2008 | Al-Ali et al. |
| 7,428,432 B2 | 9/2008 | Ali et al. |
| 7,438,683 B2 | 10/2008 | Al-Ali et al. |
| 7,440,787 B2 | 10/2008 | Diab |
| 7,454,240 B2 | 11/2008 | Diab et al. |
| 7,467,002 B2 | 12/2008 | Weber et al. |
| 7,469,157 B2 | 12/2008 | Diab et al. |
| 7,471,969 B2 | 12/2008 | Diab et al. |
| 7,471,971 B2 | 12/2008 | Diab et al. |
| 7,483,729 B2 | 1/2009 | Al-Ali et al. |
| 7,483,730 B2 | 1/2009 | Diab et al. |
| 7,489,958 B2 | 2/2009 | Diab et al. |
| 7,496,391 B2 | 2/2009 | Diab et al. |
| 7,496,393 B2 | 2/2009 | Diab et al. |
| D587,657 S | 3/2009 | Al-Ali et al. |
| 7,499,741 B2 | 3/2009 | Diab et al. |
| 7,499,835 B2 | 3/2009 | Weber et al. |
| 7,500,950 B2 | 3/2009 | Al-Ali et al. |
| 7,509,154 B2 | 3/2009 | Diab et al. |
| 7,509,494 B2 | 3/2009 | Al-Ali |
| 7,510,849 B2 | 3/2009 | Schurman et al. |
| 7,526,328 B2 | 4/2009 | Diab et al. |
| 7,530,942 B1 | 5/2009 | Diab |
| 7,530,949 B2 | 5/2009 | Al Ali et al. |
| 7,530,955 B2 | 5/2009 | Diab et al. |
| 7,563,110 B2 | 7/2009 | Al-Ali et al. |
| 7,596,398 B2 | 9/2009 | Al-Ali et al. |
| 7,618,375 B2 | 11/2009 | Flaherty |
| D606,659 S | 12/2009 | Kiani et al. |
| 7,647,083 B2 | 1/2010 | Al-Ali et al. |
| D609,193 S | 2/2010 | Al-Ali et al. |
| D614,305 S | 4/2010 | Al-Ali et al. |
| RE41,317 E | 5/2010 | Parker |
| 7,729,733 B2 | 6/2010 | Al-Ali et al. |
| 7,734,320 B2 | 6/2010 | Al-Ali |
| 7,761,127 B2 | 7/2010 | Al-Ali et al. |
| 7,761,128 B2 | 7/2010 | Al-Ali et al. |
| 7,764,982 B2 | 7/2010 | Dalke et al. |
| D621,516 S | 8/2010 | Kiani et al. |
| 7,791,155 B2 | 9/2010 | Diab |
| 7,801,581 B2 | 9/2010 | Diab |
| 7,822,452 B2 | 10/2010 | Schurman et al. |
| RE41,912 E | 11/2010 | Parker |
| 7,844,313 B2 | 11/2010 | Kiani et al. |
| 7,844,314 B2 | 11/2010 | Al-Ali |
| 7,844,315 B2 | 11/2010 | Al-Ali |
| 7,865,222 B2 | 1/2011 | Weber et al. |
| 7,873,497 B2 | 1/2011 | Weber et al. |
| 7,880,606 B2 | 2/2011 | Al-Ali |
| 7,880,626 B2 | 2/2011 | Al-Ali et al. |
| 7,891,355 B2 | 2/2011 | Al-Ali et al. |
| 7,894,868 B2 | 2/2011 | Al-Ali et al. |
| 7,899,507 B2 | 3/2011 | Al-Ali et al. |
| 7,899,518 B2 | 3/2011 | Trepagnier et al. |
| 7,904,132 B2 | 3/2011 | Weber et al. |
| 7,909,772 B2 | 3/2011 | Popov et al. |
| 7,910,875 B2 | 3/2011 | Al-Ali |
| 7,919,713 B2 | 4/2011 | Al-Ali et al. |
| 7,937,128 B2 | 5/2011 | Al-Ali |
| 7,937,129 B2 | 5/2011 | Mason et al. |

(56) References Cited

U.S. PATENT DOCUMENTS

| | | |
|---|---|---|
| 7,937,130 B2 | 5/2011 | Diab et al. |
| 7,941,199 B2 | 5/2011 | Kiani |
| 7,951,086 B2 | 5/2011 | Flaherty et al. |
| 7,957,780 B2 | 6/2011 | Lamego et al. |
| 7,962,188 B2 | 6/2011 | Kiani et al. |
| 7,962,190 B1 | 6/2011 | Diab et al. |
| 7,976,472 B2 | 7/2011 | Kiani |
| 7,988,637 B2 | 8/2011 | Diab |
| 7,990,382 B2 | 8/2011 | Kiani |
| 7,991,446 B2 | 8/2011 | Al-Ali et al. |
| 8,000,761 B2 | 8/2011 | Al-Ali |
| 8,008,088 B2 | 8/2011 | Bellott et al. |
| RE42,753 E | 9/2011 | Kiani-Azarbayjany et al. |
| 8,019,400 B2 | 9/2011 | Diab et al. |
| 8,028,701 B2 | 10/2011 | Al-Ali et al. |
| 8,029,765 B2 | 10/2011 | Bellott et al. |
| 8,036,727 B2 | 10/2011 | Schurman et al. |
| 8,036,728 B2 | 10/2011 | Diab et al. |
| 8,046,040 B2 | 10/2011 | Ali et al. |
| 8,046,041 B2 | 10/2011 | Diab et al. |
| 8,046,042 B2 | 10/2011 | Diab et al. |
| 8,048,040 B2 | 11/2011 | Kiani |
| 8,050,728 B2 | 11/2011 | Al-Ali et al. |
| RE43,169 E | 2/2012 | Parker |
| 8,118,620 B2 | 2/2012 | Al-Ali et al. |
| 8,126,528 B2 | 2/2012 | Diab et al. |
| 8,128,572 B2 | 3/2012 | Diab et al. |
| 8,130,105 B2 | 3/2012 | Al-Ali et al. |
| 8,145,287 B2 | 3/2012 | Diab et al. |
| 8,150,487 B2 | 4/2012 | Diab et al. |
| 8,175,672 B2 | 5/2012 | Parker |
| 8,180,420 B2 | 5/2012 | Diab et al. |
| 8,182,443 B1 | 5/2012 | Kiani |
| 8,185,180 B2 | 5/2012 | Diab et al. |
| 8,187,195 B2 | 5/2012 | Tulkki |
| 8,190,223 B2 | 5/2012 | Al-Ali et al. |
| 8,190,227 B2 | 5/2012 | Diab et al. |
| 8,198,861 B2 * | 6/2012 | Kudou ............... H01R 13/6205 320/114 |
| 8,203,438 B2 | 6/2012 | Kiani et al. |
| 8,203,704 B2 | 6/2012 | Merritt et al. |
| 8,204,566 B2 | 6/2012 | Schurman et al. |
| 8,219,172 B2 | 7/2012 | Schurman et al. |
| 8,224,411 B2 | 7/2012 | Al-Ali et al. |
| 8,228,181 B2 | 7/2012 | Al-Ali |
| 8,229,533 B2 | 7/2012 | Diab et al. |
| 8,233,955 B2 | 7/2012 | Al-Ali et al. |
| 8,244,325 B2 | 8/2012 | Al-Ali et al. |
| 8,255,026 B1 | 8/2012 | Al-Ali |
| 8,255,027 B2 | 8/2012 | Al-Ali et al. |
| 8,255,028 B2 | 8/2012 | Al-Ali et al. |
| 8,260,577 B2 | 9/2012 | Weber et al. |
| 8,265,723 B1 | 9/2012 | McHale et al. |
| 8,274,360 B2 | 9/2012 | Sampath et al. |
| 8,280,473 B2 | 10/2012 | Al-Ali |
| 8,301,217 B2 | 10/2012 | Al-Ali et al. |
| 8,306,596 B2 | 11/2012 | Schurman et al. |
| 8,310,336 B2 | 11/2012 | Muhsin et al. |
| 8,315,683 B2 | 11/2012 | Al-Ali et al. |
| RE43,860 E | 12/2012 | Parker |
| 8,337,403 B2 | 12/2012 | Al-Ali et al. |
| 8,346,330 B2 | 1/2013 | Lamego |
| 8,353,842 B2 | 1/2013 | Al-Ali et al. |
| 8,355,766 B2 | 1/2013 | MacNeish, III et al. |
| 8,359,080 B2 | 1/2013 | Diab et al. |
| 8,364,223 B2 | 1/2013 | Al-Ali et al. |
| 8,364,226 B2 | 1/2013 | Diab et al. |
| 8,374,665 B2 | 2/2013 | Lamego |
| 8,385,995 B2 | 2/2013 | Al-ali et al. |
| 8,385,996 B2 | 2/2013 | Smith et al. |
| 8,388,353 B2 | 3/2013 | Kiani et al. |
| 8,399,822 B2 | 3/2013 | Al-Ali |
| 8,401,602 B2 | 3/2013 | Kiani |
| 8,405,608 B2 | 3/2013 | Al-Ali et al. |
| 8,414,499 B2 | 4/2013 | Al-Ali et al. |
| 8,418,524 B2 | 4/2013 | Al-Ali |
| 8,423,106 B2 | 4/2013 | Lamego et al. |
| 8,428,967 B2 | 4/2013 | Olsen et al. |
| 8,430,817 B1 | 4/2013 | Al-Ali et al. |
| 8,437,825 B2 | 5/2013 | Dalvi et al. |
| 8,455,290 B2 | 6/2013 | Siskavich |
| 8,457,703 B2 | 6/2013 | Al-Ali |
| 8,457,707 B2 | 6/2013 | Kiani |
| 8,463,349 B2 | 6/2013 | Diab et al. |
| 8,466,286 B2 | 6/2013 | Bellot et al. |
| 8,471,713 B2 | 6/2013 | Poeze et al. |
| 8,473,020 B2 | 6/2013 | Kiani et al. |
| 8,483,787 B2 | 7/2013 | Al-Ali et al. |
| 8,489,364 B2 | 7/2013 | Weber et al. |
| 8,497,753 B2 | 7/2013 | DiFonzo et al. |
| 8,498,684 B2 | 7/2013 | Weber et al. |
| 8,504,128 B2 | 8/2013 | Blank et al. |
| 8,509,867 B2 | 8/2013 | Workman et al. |
| 8,515,509 B2 | 8/2013 | Bruinsma et al. |
| 8,523,781 B2 | 9/2013 | Al-Ali |
| 8,529,301 B2 | 9/2013 | Al-Ali et al. |
| 8,532,727 B2 | 9/2013 | Ali et al. |
| 8,532,728 B2 | 9/2013 | Diab et al. |
| D692,145 S | 10/2013 | Al-Ali et al. |
| 8,547,209 B2 | 10/2013 | Kiani et al. |
| 8,548,548 B2 | 10/2013 | Al-Ali |
| 8,548,549 B2 | 10/2013 | Schurman et al. |
| 8,548,550 B2 | 10/2013 | Al-Ali et al. |
| 8,560,032 B2 | 10/2013 | Al-Ali et al. |
| 8,560,034 B1 | 10/2013 | Diab et al. |
| 8,570,167 B2 | 10/2013 | Al-Ali |
| 8,570,503 B2 | 10/2013 | Vo et al. |
| 8,571,617 B2 | 10/2013 | Reichgott et al. |
| 8,571,618 B1 | 10/2013 | Lamego et al. |
| 8,571,619 B2 | 10/2013 | Al-Ali et al. |
| 8,577,431 B2 | 11/2013 | Lamego et al. |
| 8,581,732 B2 | 11/2013 | Al-Ali et al. |
| 8,584,345 B2 | 11/2013 | Al-Ali et al. |
| 8,588,880 B2 | 11/2013 | Abdul-Hafiz et al. |
| 8,600,467 B2 | 12/2013 | Al-Ali et al. |
| 8,606,342 B2 | 12/2013 | Diab |
| 8,626,255 B2 | 1/2014 | Al-Ali et al. |
| 8,630,691 B2 | 1/2014 | Lamego et al. |
| 8,634,889 B2 | 1/2014 | Al-Ali et al. |
| 8,641,631 B2 | 2/2014 | Sierra et al. |
| 8,652,060 B2 | 2/2014 | Al-Ali |
| 8,663,107 B2 | 3/2014 | Kiani |
| 8,666,468 B1 | 3/2014 | Al-Ali |
| 8,667,967 B2 | 3/2014 | Al-Ali et al. |
| 8,670,811 B2 | 3/2014 | O'Reilly |
| 8,670,814 B2 | 3/2014 | Diab et al. |
| 8,676,286 B2 | 3/2014 | Weber et al. |
| 8,682,407 B2 | 3/2014 | Al-Ali |
| RE44,823 E | 4/2014 | Parker |
| RE44,875 E | 4/2014 | Kiani et al. |
| 8,690,799 B2 | 4/2014 | Telfort et al. |
| 8,700,112 B2 | 4/2014 | Kiani |
| 8,702,627 B2 | 4/2014 | Telfort et al. |
| 8,706,179 B2 | 4/2014 | Parker |
| 8,712,494 B1 | 4/2014 | MacNeish, III et al. |
| 8,715,206 B2 | 5/2014 | Telfort et al. |
| 8,718,735 B2 | 5/2014 | Lamego et al. |
| 8,718,737 B2 | 5/2014 | Diab et al. |
| 8,718,738 B2 | 5/2014 | Blank et al. |
| 8,720,249 B2 | 5/2014 | Al-Ali |
| 8,721,541 B2 | 5/2014 | Al-Ali et al. |
| 8,721,542 B2 | 5/2014 | Al-Ali et al. |
| 8,723,677 B1 | 5/2014 | Kiani |
| 8,740,792 B1 | 6/2014 | Kiani et al. |
| 8,754,776 B2 | 6/2014 | Poeze et al. |
| 8,755,535 B2 | 6/2014 | Telfort et al. |
| 8,755,856 B2 | 6/2014 | Diab et al. |
| 8,755,872 B1 | 6/2014 | Marinow |
| 8,761,850 B2 | 6/2014 | Lamego |
| 8,764,671 B2 | 7/2014 | Kiani |
| 8,768,423 B2 | 7/2014 | Shakespeare et al. |
| 8,771,204 B2 | 7/2014 | Telfort et al. |
| 8,777,634 B2 | 7/2014 | Kiani et al. |
| 8,781,543 B2 | 7/2014 | Diab et al. |

(56) References Cited

U.S. PATENT DOCUMENTS

| | | |
|---|---|---|
| 8,781,544 B2 | 7/2014 | Al-Ali et al. |
| 8,781,549 B2 | 7/2014 | Al-Ali et al. |
| 8,788,003 B2 | 7/2014 | Schurman et al. |
| 8,790,268 B2 | 7/2014 | Al-Ali |
| 8,801,613 B2 | 8/2014 | Al-Ali et al. |
| 8,821,397 B2 | 9/2014 | Al-Ali et al. |
| 8,821,415 B2 | 9/2014 | Al-Ali et al. |
| 8,830,449 B1 | 9/2014 | Lamego et al. |
| 8,831,700 B2 | 9/2014 | Schurman et al. |
| 8,840,549 B2 | 9/2014 | Al-Ali et al. |
| 8,847,740 B2 | 9/2014 | Kiani et al. |
| 8,849,365 B2 | 9/2014 | Smith et al. |
| 8,852,094 B2 | 10/2014 | Al-Ali et al. |
| 8,852,994 B2 | 10/2014 | Wojtczuk et al. |
| 8,868,147 B2 | 10/2014 | Stippick et al. |
| 8,868,150 B2 | 10/2014 | Al-Ali et al. |
| 8,870,792 B2 | 10/2014 | Al-Ali et al. |
| 8,886,271 B2 | 11/2014 | Kiani et al. |
| 8,888,539 B2 | 11/2014 | Al-Ali et al. |
| 8,888,708 B2 | 11/2014 | Diab et al. |
| 8,892,180 B2 | 11/2014 | Weber et al. |
| 8,897,847 B2 | 11/2014 | Al-Ali |
| 8,909,310 B2 | 12/2014 | Lamego et al. |
| 8,911,377 B2 | 12/2014 | Al-Ali |
| 8,912,909 B2 | 12/2014 | Al-Ali et al. |
| 8,920,317 B2 | 12/2014 | Al-Ali et al. |
| 8,921,699 B2 | 12/2014 | Al-Ali et al. |
| 8,922,382 B2 | 12/2014 | Al-Ali et al. |
| 8,929,964 B2 | 1/2015 | Al-Ali et al. |
| 8,942,777 B2 | 1/2015 | Diab et al. |
| 8,948,834 B2 | 2/2015 | Diab et al. |
| 8,948,835 B2 | 2/2015 | Diab |
| 8,965,471 B2 | 2/2015 | Lamego |
| 8,983,564 B2 | 3/2015 | Al-Ali |
| 8,989,831 B2 | 3/2015 | Al-Ali et al. |
| 8,996,085 B2 | 3/2015 | Kiani et al. |
| 8,998,809 B2 | 4/2015 | Kiani |
| 9,028,429 B2 | 5/2015 | Telfort et al. |
| 9,037,207 B2 | 5/2015 | Al-Ali et al. |
| 9,060,721 B2 | 6/2015 | Reichgott et al. |
| 9,066,666 B2 | 6/2015 | Kiani |
| 9,066,680 B1 | 6/2015 | Al-Ali et al. |
| 9,072,474 B2 | 7/2015 | Al-Ali et al. |
| 9,078,560 B2 | 7/2015 | Schurman et al. |
| 9,084,569 B2 | 7/2015 | Weber et al. |
| 9,095,316 B2 | 8/2015 | Welch et al. |
| 9,106,038 B2 | 8/2015 | Telfort et al. |
| 9,107,625 B2 | 8/2015 | Telfort et al. |
| 9,107,626 B2 | 8/2015 | Al-Ali et al. |
| 9,113,831 B2 | 8/2015 | Al-Ali |
| 9,113,832 B2 | 8/2015 | Al-Ali |
| 9,119,595 B2 | 9/2015 | Lamego |
| 9,131,881 B2 | 9/2015 | Diab et al. |
| 9,131,882 B2 | 9/2015 | Al-Ali et al. |
| 9,131,883 B2 | 9/2015 | Al-Ali |
| 9,131,917 B2 | 9/2015 | Telfort et al. |
| 9,138,180 B1 | 9/2015 | Coverston et al. |
| 9,138,182 B2 | 9/2015 | Al-Ali et al. |
| 9,138,192 B2 | 9/2015 | Weber et al. |
| 9,142,117 B2 | 9/2015 | Muhsin et al. |
| 9,153,112 B1 | 10/2015 | Kiani et al. |
| 9,153,121 B2 | 10/2015 | Kiani et al. |
| 9,161,696 B2 | 10/2015 | Al-Ali et al. |
| 9,161,713 B2 | 10/2015 | Al-Ali et al. |
| 9,167,995 B2 | 10/2015 | Lamego et al. |
| 9,176,141 B2 | 11/2015 | Al-Ali et al. |
| 9,186,102 B2 | 11/2015 | Bruinsma et al. |
| 9,192,312 B2 | 11/2015 | Al-Ali |
| 9,192,329 B2 | 11/2015 | Al-Ali |
| 9,192,351 B1 | 11/2015 | Telfort et al. |
| 9,195,385 B2 | 11/2015 | Al-Ali et al. |
| 9,211,072 B2 | 12/2015 | Kiani |
| 9,211,095 B1 | 12/2015 | Al-Ali |
| 9,218,454 B2 | 12/2015 | Kiani et al. |
| 9,226,696 B2 | 1/2016 | Kiani |
| 9,241,662 B2 | 1/2016 | Al-Ali et al. |
| 9,245,668 B1 | 1/2016 | Vo et al. |
| 9,259,185 B2 | 2/2016 | Abdul-Hafiz et al. |
| 9,267,572 B2 | 2/2016 | Barker et al. |
| 9,277,880 B2 | 3/2016 | Poeze et al. |
| 9,289,167 B2 | 3/2016 | Diab et al. |
| 9,295,421 B2 | 3/2016 | Kiani et al. |
| 9,307,928 B1 | 4/2016 | Al-Ali et al. |
| 9,323,894 B2 | 4/2016 | Kiani |
| D755,392 S | 5/2016 | Hwang et al. |
| 9,326,712 B1 | 5/2016 | Kiani |
| 9,333,316 B2 | 5/2016 | Kiani |
| 9,339,220 B2 | 5/2016 | Lamego et al. |
| 9,341,565 B2 | 5/2016 | Lamego et al. |
| 9,351,673 B2 | 5/2016 | Diab et al. |
| 9,351,675 B2 | 5/2016 | Al-Ali et al. |
| 9,364,181 B2 | 6/2016 | Kiani et al. |
| 9,368,671 B2 | 6/2016 | Wojtczuk et al. |
| 9,370,325 B2 | 6/2016 | Al-Ali et al. |
| 9,370,326 B2 | 6/2016 | McHale et al. |
| 9,370,335 B2 | 6/2016 | Al-ali et al. |
| 9,375,185 B2 | 6/2016 | Ali et al. |
| 9,386,953 B2 | 7/2016 | Al-Ali |
| 9,386,961 B2 | 7/2016 | Al-Ali et al. |
| 9,392,945 B2 | 7/2016 | Al-Ali et al. |
| 9,397,448 B2 | 7/2016 | Al-Ali et al. |
| 9,408,542 B1 | 8/2016 | Kinast et al. |
| 9,436,645 B2 | 9/2016 | Al-Ali et al. |
| 9,445,759 B1 | 9/2016 | Lamego et al. |
| 9,466,919 B2 | 10/2016 | Kiani et al. |
| 9,474,474 B2 | 10/2016 | Lamego et al. |
| 9,480,422 B2 | 11/2016 | Al-Ali |
| 9,480,435 B2 | 11/2016 | Olsen |
| 9,492,110 B2 | 11/2016 | Al-Ali et al. |
| 9,510,779 B2 | 12/2016 | Poeze et al. |
| 9,517,024 B2 | 12/2016 | Kiani et al. |
| 9,532,722 B2 | 1/2017 | Lamego et al. |
| 9,538,949 B2 | 1/2017 | Al-Ali et al. |
| 9,538,980 B2 | 1/2017 | Telfort et al. |
| 9,549,696 B2 | 1/2017 | Lamego et al. |
| 9,554,737 B2 | 1/2017 | Schurman et al. |
| 9,560,996 B2 | 2/2017 | Kiani |
| 9,560,998 B2 | 2/2017 | Al-Ali et al. |
| 9,566,019 B2 | 2/2017 | Al-Ali et al. |
| 9,579,039 B2 | 2/2017 | Jansen et al. |
| 9,591,975 B2 | 3/2017 | Dalvi et al. |
| 9,614,337 B2 | 4/2017 | Lisogurski et al. |
| 9,622,692 B2 | 4/2017 | Lamego et al. |
| 9,622,693 B2 | 4/2017 | Diab |
| D788,312 S | 5/2017 | Al-Ali et al. |
| 9,636,055 B2 | 5/2017 | Al-Ali et al. |
| 9,636,056 B2 | 5/2017 | Al-Ali |
| 9,649,054 B2 | 5/2017 | Lamego et al. |
| 9,662,052 B2 | 5/2017 | Al-Ali et al. |
| 9,668,679 B2 | 6/2017 | Schurman et al. |
| 9,668,680 B2 | 6/2017 | Bruinsma et al. |
| 9,668,703 B2 | 6/2017 | Al-Ali |
| 9,675,286 B2 | 6/2017 | Diab |
| 9,687,160 B2 | 6/2017 | Kiani |
| 9,693,719 B2 | 7/2017 | Al-Ali et al. |
| 9,693,737 B2 | 7/2017 | Al-Ali |
| 9,697,928 B2 | 7/2017 | Al-Ali et al. |
| 9,717,425 B2 | 8/2017 | Kiani et al. |
| 9,717,458 B2 | 8/2017 | Lamego et al. |
| 9,724,016 B1 | 8/2017 | Al-Ali et al. |
| 9,724,024 B2 | 8/2017 | Al-Ali |
| 9,724,025 B1 | 8/2017 | Kiani et al. |
| 9,730,640 B2 | 8/2017 | Diab et al. |
| 9,743,887 B2 | 8/2017 | Al-Ali et al. |
| 9,749,232 B2 | 8/2017 | Sampath et al. |
| 9,750,442 B2 | 9/2017 | Olsen |
| 9,750,443 B2 | 9/2017 | Smith et al. |
| 9,750,461 B1 | 9/2017 | Telfort |
| 9,775,545 B2 | 10/2017 | Al-Ali et al. |
| 9,775,546 B2 | 10/2017 | Diab et al. |
| 9,775,570 B2 | 10/2017 | Al-Ali |
| 9,778,079 B1 | 10/2017 | Al-Ali et al. |
| 9,782,077 B2 | 10/2017 | Lamego et al. |
| 9,782,110 B2 | 10/2017 | Kiani |

(56) References Cited

U.S. PATENT DOCUMENTS

| | | |
|---|---|---|
| 9,787,568 B2 | 10/2017 | Lamego et al. |
| 9,788,735 B2 | 10/2017 | Al-Ali |
| 9,788,768 B2 | 10/2017 | Al-Ali et al. |
| 9,795,300 B2 | 10/2017 | Al-Ali |
| 9,795,310 B2 | 10/2017 | Al-Ali |
| 9,795,358 B2 | 10/2017 | Telfort et al. |
| 9,795,739 B2 | 10/2017 | Al-Ali et al. |
| 9,801,556 B2 | 10/2017 | Kiani |
| 9,801,588 B2 | 10/2017 | Weber et al. |
| 9,808,188 B1 | 11/2017 | Perea et al. |
| 9,814,418 B2 | 11/2017 | Weber et al. |
| 9,820,691 B2 | 11/2017 | Kiani |
| 9,833,152 B2 | 12/2017 | Kiani et al. |
| 9,833,180 B2 | 12/2017 | Shakespeare et al. |
| 9,839,379 B2 | 12/2017 | Al-Ali et al. |
| 9,839,381 B1 | 12/2017 | Weber et al. |
| 9,847,002 B2 | 12/2017 | Kiani et al. |
| 9,847,749 B2 | 12/2017 | Kiani et al. |
| 9,848,800 B1 | 12/2017 | Lee et al. |
| 9,848,806 B2 | 12/2017 | Al-Ali et al. |
| 9,848,807 B2 | 12/2017 | Lamego |
| 9,861,298 B2 | 1/2018 | Eckerbom et al. |
| 9,861,304 B2 | 1/2018 | Al-Ali et al. |
| 9,861,305 B1 | 1/2018 | Weber et al. |
| 9,867,578 B2 | 1/2018 | Al-Ali et al. |
| 9,872,623 B2 | 1/2018 | Al-Ali |
| 9,876,320 B2 | 1/2018 | Coverston et al. |
| 9,877,650 B2 | 1/2018 | Muhsin et al. |
| 9,877,686 B2 | 1/2018 | Al-Ali et al. |
| 9,891,079 B2 | 2/2018 | Dalvi |
| 9,895,107 B2 | 2/2018 | Al-Ali et al. |
| 9,913,617 B2 | 3/2018 | Al-Ali et al. |
| 9,924,893 B2 | 3/2018 | Schurman et al. |
| 9,924,897 B1 | 3/2018 | Abdul-Hafiz |
| 9,936,917 B2 | 4/2018 | Poeze et al. |
| 9,943,269 B2 | 4/2018 | Muhsin et al. |
| 9,949,676 B2 | 4/2018 | Al-Ali |
| 9,955,937 B2 | 5/2018 | Telfort |
| 9,965,946 B2 | 5/2018 | Al-Ali |
| 9,980,667 B2 | 5/2018 | Kiani et al. |
| D820,865 S | 6/2018 | Muhsin et al. |
| 9,986,919 B2 | 6/2018 | Lamego et al. |
| 9,986,952 B2 | 6/2018 | Dalvi et al. |
| 9,989,560 B2 | 6/2018 | Poeze et al. |
| 9,993,207 B2 | 6/2018 | Al-Ali et al. |
| 10,007,758 B2 | 6/2018 | Al-Ali et al. |
| D822,215 S | 7/2018 | Al-Ali et al. |
| D822,216 S | 7/2018 | Barker et al. |
| 10,010,276 B2 | 7/2018 | Al-Ali et al. |
| 10,032,002 B2 | 7/2018 | Kiani et al. |
| 10,039,482 B2 | 8/2018 | Al-Ali et al. |
| 10,052,037 B2 | 8/2018 | Kinast et al. |
| 10,058,275 B2 | 8/2018 | Al-Ali et al. |
| 10,064,562 B2 | 9/2018 | Al-Ali |
| 10,086,138 B1 | 10/2018 | Novak, Jr. |
| 10,092,200 B2 | 10/2018 | Al-Ali et al. |
| 10,092,249 B2 | 10/2018 | Kiani et al. |
| 10,098,550 B2 | 10/2018 | Al-Ali et al. |
| 10,098,591 B2 | 10/2018 | Al-Ali et al. |
| 10,098,610 B2 | 10/2018 | Al-Ali et al. |
| D833,624 S | 11/2018 | DeJong et al. |
| 10,123,726 B2 | 11/2018 | Al-Ali et al. |
| 10,130,289 B2 | 11/2018 | Al-Ali et al. |
| 10,130,291 B2 | 11/2018 | Schurman et al. |
| D835,282 S | 12/2018 | Barker et al. |
| D835,283 S | 12/2018 | Barker et al. |
| D835,284 S | 12/2018 | Barker et al. |
| D835,285 S | 12/2018 | Barker et al. |
| 10,149,616 B2 | 12/2018 | Al-Ali et al. |
| 10,154,815 B2 | 12/2018 | Al-Ali et al. |
| 10,159,412 B2 | 12/2018 | Lamego et al. |
| 10,188,296 B2 | 1/2019 | Al-Ali et al. |
| 10,188,331 B1 | 1/2019 | Al-Ali et al. |
| 10,188,348 B2 | 1/2019 | Kiani et al. |
| RE47,218 E | 2/2019 | Ali-Ali |
| RE47,244 E | 2/2019 | Kiani et al. |
| RE47,249 E | 2/2019 | Kiani et al. |
| 10,194,847 B2 | 2/2019 | Al-Ali |
| 10,194,848 B1 | 2/2019 | Kiani et al. |
| 10,201,298 B2 | 2/2019 | Al-Ali et al. |
| 10,205,272 B2 | 2/2019 | Kiani et al. |
| 10,205,291 B2 | 2/2019 | Scruggs et al. |
| 10,213,108 B2 | 2/2019 | Al-Ali |
| 10,219,706 B2 | 3/2019 | Al-Ali |
| 10,219,746 B2 | 3/2019 | McHale et al. |
| 10,226,576 B2 | 3/2019 | Kiani |
| 10,231,657 B2 | 3/2019 | Al-Ali et al. |
| 10,231,670 B2 | 3/2019 | Blank et al. |
| 10,231,676 B2 | 3/2019 | Al-Ali et al. |
| 2006/0161054 A1 | 7/2006 | Reuss et al. |
| 2007/0072443 A1* | 3/2007 | Rohrbach ............ G06F 1/1633 439/39 |
| 2007/0282478 A1 | 12/2007 | Al-Ali et al. |
| 2009/0111287 A1* | 4/2009 | Lindberg ........... H01R 13/6205 439/39 |
| 2009/0247984 A1 | 10/2009 | Lamego et al. |
| 2009/0275813 A1 | 11/2009 | Davis |
| 2009/0275844 A1 | 11/2009 | Al-Ali |
| 2010/0004518 A1 | 1/2010 | Vo et al. |
| 2010/0030040 A1 | 2/2010 | Poeze et al. |
| 2011/0082711 A1 | 4/2011 | Poeze et al. |
| 2011/0125060 A1 | 5/2011 | Telfort et al. |
| 2011/0208015 A1 | 8/2011 | Welch et al. |
| 2011/0230733 A1 | 9/2011 | Al-Ali |
| 2012/0165629 A1 | 6/2012 | Merritt et al. |
| 2012/0209082 A1 | 8/2012 | Al-Ali |
| 2012/0209084 A1 | 8/2012 | Olsen et al. |
| 2012/0283524 A1 | 11/2012 | Kiani et al. |
| 2013/0023775 A1 | 1/2013 | Lamego et al. |
| 2013/0041591 A1 | 2/2013 | Lamego |
| 2013/0060147 A1 | 3/2013 | Welch et al. |
| 2013/0096405 A1 | 4/2013 | Garfio |
| 2013/0096936 A1 | 4/2013 | Sampath et al. |
| 2013/0243021 A1 | 9/2013 | Siskavich |
| 2013/0253334 A1 | 9/2013 | Al-Ali et al. |
| 2013/0296672 A1 | 11/2013 | O'Neil et al. |
| 2013/0296713 A1 | 11/2013 | Al-Ali et al. |
| 2013/0324808 A1 | 12/2013 | Al-Ali et al. |
| 2013/0331660 A1 | 12/2013 | Al-Ali et al. |
| 2014/0012100 A1 | 1/2014 | Al-Ali et al. |
| 2014/0051953 A1 | 2/2014 | Lamego et al. |
| 2014/0120564 A1 | 5/2014 | Workman et al. |
| 2014/0121482 A1 | 5/2014 | Merritt et al. |
| 2014/0127137 A1 | 5/2014 | Bellott et al. |
| 2014/0163344 A1 | 6/2014 | Al-Ali |
| 2014/0166076 A1 | 6/2014 | Kiani et al. |
| 2014/0171763 A1 | 6/2014 | Diab |
| 2014/0180038 A1 | 6/2014 | Kiani |
| 2014/0180154 A1 | 6/2014 | Sierra et al. |
| 2014/0180160 A1 | 6/2014 | Brown et al. |
| 2014/0187973 A1 | 7/2014 | Brown et al. |
| 2014/0213864 A1 | 7/2014 | Abdul-Hafiz et al. |
| 2014/0275835 A1 | 9/2014 | Lamego et al. |
| 2014/0275871 A1 | 9/2014 | Lamego et al. |
| 2014/0275872 A1 | 9/2014 | Merritt et al. |
| 2014/0288400 A1 | 9/2014 | Diab et al. |
| 2014/0316217 A1 | 10/2014 | Purdon et al. |
| 2014/0316218 A1 | 10/2014 | Purdon et al. |
| 2014/0316228 A1 | 10/2014 | Blank et al. |
| 2014/0323825 A1 | 10/2014 | Al-Ali et al. |
| 2014/0323897 A1 | 10/2014 | Brown et al. |
| 2014/0323898 A1 | 10/2014 | Purdon et al. |
| 2014/0330092 A1 | 11/2014 | Al-Ali et al. |
| 2014/0330098 A1 | 11/2014 | Merritt et al. |
| 2014/0357966 A1 | 12/2014 | Al-Ali et al. |
| 2015/0005600 A1 | 1/2015 | Blank et al. |
| 2015/0011907 A1 | 1/2015 | Purdon et al. |
| 2015/0032029 A1 | 1/2015 | Al-Ali et al. |
| 2015/0038859 A1 | 2/2015 | Dalvi et al. |
| 2015/0080754 A1 | 3/2015 | Purdon et al. |
| 2015/0087936 A1 | 3/2015 | Al-Ali et al. |
| 2015/0094546 A1 | 4/2015 | Al-Ali |
| 2015/0099950 A1 | 4/2015 | Al-Ali et al. |
| 2015/0101844 A1 | 4/2015 | Al-Ali et al. |

(56) References Cited

U.S. PATENT DOCUMENTS

| | | |
|---|---|---|
| 2015/0106121 A1 | 4/2015 | Muhsin et al. |
| 2015/0112151 A1 | 4/2015 | Muhsin et al. |
| 2015/0133755 A1 | 5/2015 | Smith et al. |
| 2015/0165312 A1 | 6/2015 | Kiani |
| 2015/0196249 A1 | 7/2015 | Brown et al. |
| 2015/0216459 A1 | 8/2015 | Al-Ali et al. |
| 2015/0238722 A1 | 8/2015 | Al-Ali |
| 2015/0245773 A1 | 9/2015 | Lamego et al. |
| 2015/0245794 A1 | 9/2015 | Al-Ali |
| 2015/0257689 A1 | 9/2015 | Al-Ali et al. |
| 2015/0272514 A1 | 10/2015 | Kiani et al. |
| 2015/0351697 A1 | 12/2015 | Weber et al. |
| 2015/0359429 A1 | 12/2015 | Al-Ali et al. |
| 2015/0366507 A1 | 12/2015 | Blank |
| 2016/0029932 A1 | 2/2016 | Al-Ali |
| 2016/0058347 A1 | 3/2016 | Reichgott et al. |
| 2016/0066824 A1 | 3/2016 | Al-Ali et al. |
| 2016/0081552 A1 | 3/2016 | Wojtczuk et al. |
| 2016/0095543 A1 | 4/2016 | Telfort et al. |
| 2016/0095548 A1 | 4/2016 | Al-Ali et al. |
| 2016/0103598 A1 | 4/2016 | Al-Ali et al. |
| 2016/0166182 A1 | 6/2016 | Al-Ali et al. |
| 2016/0166183 A1 | 6/2016 | Poeze et al. |
| 2016/0196388 A1 | 7/2016 | Lamego |
| 2016/0197436 A1 | 7/2016 | Barker et al. |
| 2016/0213281 A1 | 7/2016 | Eckerbom et al. |
| 2016/0228043 A1 | 8/2016 | O'Neil et al. |
| 2016/0233632 A1 | 8/2016 | Scruggs et al. |
| 2016/0234944 A1 | 8/2016 | Schmidt et al. |
| 2016/0270735 A1 | 9/2016 | Diab et al. |
| 2016/0283665 A1 | 9/2016 | Sampath et al. |
| 2016/0287090 A1 | 10/2016 | Al-Ali et al. |
| 2016/0287786 A1 | 10/2016 | Kiani |
| 2016/0296169 A1 | 10/2016 | McHale et al. |
| 2016/0310052 A1 | 10/2016 | Al-Ali et al. |
| 2016/0314260 A1 | 10/2016 | Kiani |
| 2016/0324488 A1 | 11/2016 | Olsen |
| 2016/0327984 A1 | 11/2016 | Al-Ali et al. |
| 2016/0331332 A1 | 11/2016 | Al-Ali |
| 2016/0367173 A1 | 12/2016 | Dalvi et al. |
| 2017/0000394 A1 | 1/2017 | Al-Ali et al. |
| 2017/0007134 A1 | 1/2017 | Al-Ali et al. |
| 2017/0007198 A1 | 1/2017 | Al-Ali et al. |
| 2017/0014083 A1 | 1/2017 | Diab et al. |
| 2017/0014084 A1 | 1/2017 | Al-Ali et al. |
| 2017/0024748 A1 | 1/2017 | Haider |
| 2017/0042488 A1 | 2/2017 | Muhsin |
| 2017/0055851 A1 | 3/2017 | Al-Ali |
| 2017/0055882 A1 | 3/2017 | Al-Ali et al. |
| 2017/0055887 A1 | 3/2017 | Al-Ali |
| 2017/0055896 A1 | 3/2017 | Al-Ali et al. |
| 2017/0079594 A1 | 3/2017 | Telfort et al. |
| 2017/0086723 A1 | 3/2017 | Al-Ali et al. |
| 2017/0143281 A1 | 5/2017 | Olsen |
| 2017/0147774 A1 | 5/2017 | Kiani |
| 2017/0156620 A1 | 6/2017 | Al-Ali et al. |
| 2017/0173632 A1 | 6/2017 | Al-Ali |
| 2017/0187146 A1 | 6/2017 | Kiani et al. |
| 2017/0188919 A1 | 7/2017 | Al-Ali et al. |
| 2017/0196464 A1 | 7/2017 | Jansen et al. |
| 2017/0196470 A1 | 7/2017 | Lamego et al. |
| 2017/0224262 A1 | 8/2017 | Al-Ali |
| 2017/0228516 A1 | 8/2017 | Sampath et al. |
| 2017/0245790 A1 | 8/2017 | Al-Ali et al. |
| 2017/0251974 A1 | 9/2017 | Shreim et al. |
| 2017/0251975 A1 | 9/2017 | Shreim et al. |
| 2017/0258403 A1 | 9/2017 | Abdul-Hafiz et al. |
| 2017/0311851 A1 | 11/2017 | Schurman et al. |
| 2017/0311891 A1 | 11/2017 | Kiani et al. |
| 2017/0325728 A1 | 11/2017 | Al-Ali et al. |
| 2017/0332976 A1 | 11/2017 | Al-Ali et al. |
| 2017/0340293 A1 | 11/2017 | Al-Ali et al. |
| 2017/0360310 A1 | 12/2017 | Kiani et al. |
| 2017/0367632 A1 | 12/2017 | Al-Ali et al. |
| 2018/0008146 A1 | 1/2018 | Al-Ali et al. |
| 2018/0013562 A1 | 1/2018 | Haider et al. |
| 2018/0014752 A1 | 1/2018 | Al-Ali et al. |
| 2018/0028124 A1 | 2/2018 | Al-Ali et al. |
| 2018/0055385 A1 | 3/2018 | Al-Ali |
| 2018/0055390 A1 | 3/2018 | Kiani et al. |
| 2018/0055430 A1 | 3/2018 | Diab et al. |
| 2018/0064381 A1 | 3/2018 | Shakespeare et al. |
| 2018/0069776 A1 | 3/2018 | Lamego et al. |
| 2018/0070867 A1 | 3/2018 | Smith et al. |
| 2018/0082767 A1 | 3/2018 | Al-Ali et al. |
| 2018/0085068 A1 | 3/2018 | Telfort |
| 2018/0087937 A1 | 3/2018 | Al-Ali et al. |
| 2018/0103874 A1 | 4/2018 | Lee et al. |
| 2018/0103905 A1 | 4/2018 | Kiani |
| 2018/0110478 A1 | 4/2018 | Al-Ali |
| 2018/0116575 A1 | 5/2018 | Perea et al. |
| 2018/0125368 A1 | 5/2018 | Lamego et al. |
| 2018/0125430 A1 | 5/2018 | Al-Ali et al. |
| 2018/0125445 A1 | 5/2018 | Telfort et al. |
| 2018/0130325 A1 | 5/2018 | Kiani et al. |
| 2018/0132769 A1 | 5/2018 | Weber et al. |
| 2018/0132770 A1 | 5/2018 | Lamego |
| 2018/0146901 A1 | 5/2018 | Al-Ali et al. |
| 2018/0146902 A1 | 5/2018 | Kiani et al. |
| 2018/0153442 A1 | 6/2018 | Eckerbom et al. |
| 2018/0153446 A1 | 6/2018 | Kiani |
| 2018/0153447 A1 | 6/2018 | Al-Ali et al. |
| 2018/0153448 A1 | 6/2018 | Weber et al. |
| 2018/0161499 A1 | 6/2018 | Al-Ali et al. |
| 2018/0168491 A1 | 6/2018 | Al-Ali et al. |
| 2018/0174679 A1 | 6/2018 | Sampath et al. |
| 2018/0174680 A1 | 6/2018 | Sampath et al. |
| 2018/0182484 A1 | 6/2018 | Sampath et al. |
| 2018/0184917 A1 | 7/2018 | Kiani |
| 2018/0192924 A1 | 7/2018 | Al-Ali |
| 2018/0192953 A1 | 7/2018 | Shreim et al. |
| 2018/0192955 A1 | 7/2018 | Al-Ali et al. |
| 2018/0199871 A1 | 7/2018 | Pauley et al. |
| 2018/0206795 A1 | 7/2018 | Al-Ali |
| 2018/0206815 A1 | 7/2018 | Telfort |
| 2018/0213583 A1 | 7/2018 | Al-Ali |
| 2018/0214031 A1 | 8/2018 | Kiani et al. |
| 2018/0214090 A1 | 8/2018 | Al-Ali et al. |
| 2018/0218792 A1 | 8/2018 | Muhsin et al. |
| 2018/0225960 A1 | 8/2018 | Al-Ali et al. |
| 2018/0238718 A1 | 8/2018 | Dalvi |
| 2018/0242853 A1 | 8/2018 | Al-Ali |
| 2018/0242921 A1 | 8/2018 | Muhsin et al. |
| 2018/0242923 A1 | 8/2018 | Al-Ali et al. |
| 2018/0242924 A1 | 8/2018 | Barker et al. |
| 2018/0242926 A1 | 8/2018 | Muhsin et al. |
| 2018/0247353 A1 | 8/2018 | Al-Ali et al. |
| 2018/0247712 A1 | 8/2018 | Muhsin et al. |
| 2018/0249933 A1 | 9/2018 | Schurman et al. |
| 2018/0253947 A1 | 9/2018 | Muhsin et al. |
| 2018/0256087 A1 | 9/2018 | Al-Ali et al. |
| 2018/0256113 A1 | 9/2018 | Weber et al. |
| 2018/0285094 A1 | 10/2018 | Housel et al. |
| 2018/0289325 A1 | 10/2018 | Poeze et al. |
| 2018/0289337 A1 | 10/2018 | Al-Ali et al. |
| 2018/0296161 A1 | 10/2018 | Shreim et al. |
| 2018/0300919 A1 | 10/2018 | Muhsin et al. |
| 2018/0310822 A1 | 11/2018 | Indorf et al. |
| 2018/0310823 A1 | 11/2018 | Al-Ali et al. |
| 2018/0317826 A1 | 11/2018 | Muhsin |
| 2018/0317841 A1 | 11/2018 | Novak, Jr. |
| 2018/0333055 A1 | 11/2018 | Lamego et al. |
| 2018/0333087 A1 | 11/2018 | Al-Ali |
| 2019/0000317 A1 | 1/2019 | Muhsin et al. |
| 2019/0000362 A1 | 1/2019 | Kiani et al. |
| 2019/0015023 A1 | 1/2019 | Monfre |
| 2019/0021638 A1 | 1/2019 | Al-Ali et al. |
| 2019/0029574 A1 | 1/2019 | Schurman et al. |
| 2019/0029578 A1 | 1/2019 | Al-Ali et al. |
| 2019/0058280 A1 | 2/2019 | Al-Ali et al. |
| 2019/0058281 A1 | 2/2019 | Al-Ali et al. |
| 2019/0069813 A1 | 3/2019 | Al-Ali |
| 2019/0069814 A1 | 3/2019 | Al-Ali |
| 2019/0076028 A1 | 3/2019 | Al-Ali et al. |

(56) References Cited

U.S. PATENT DOCUMENTS

2019/0090748 A1 3/2019 Al-Ali
2019/0090760 A1 3/2019 Kinast et al.
2019/0090764 A1 3/2019 Al-Ali

* cited by examiner

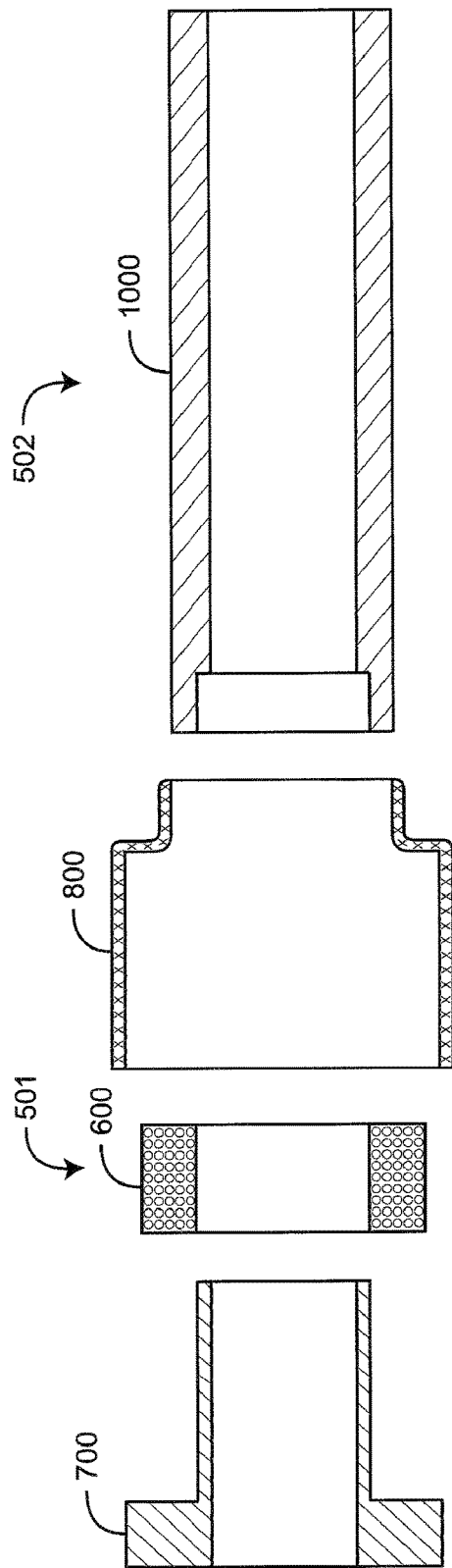
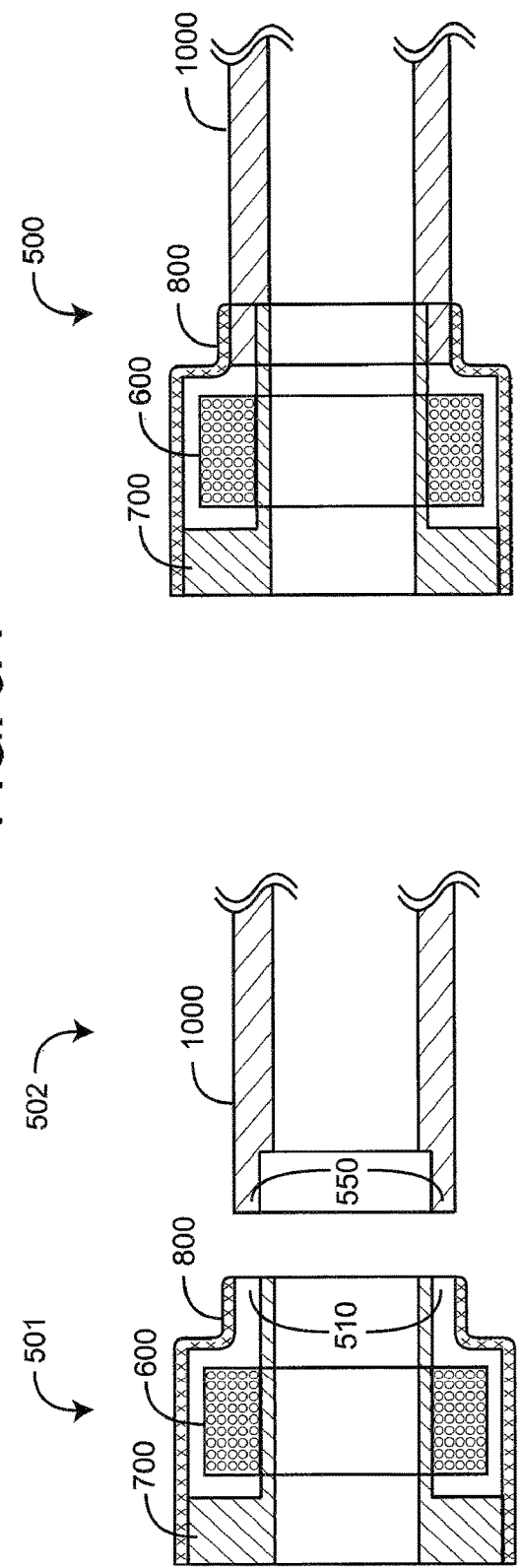
FIG. 6A
FIG. 6B
FIG. 6C

MAGNETIC CONNECTOR FOR A DATA COMMUNICATIONS CABLE

CROSS-REFERENCE TO RELATED APPLICATIONS

The present application is a continuation of U.S. patent application Ser. No. 15/288,987, filed Oct. 7, 2016, which is a continuation of U.S. patent application Ser. No. 13/783,424, filed Mar. 4, 2013, now issued as U.S. Pat. No. 9,466,919, which is a continuation of U.S. patent application Ser. No. 12/721,199, filed Mar. 10, 2010, now issued as U.S. Pat. No. 8,388,353, which claims priority benefit under 35 U.S.C. § 119(e) to U.S. Provisional Patent Application Ser. No. 61/159,336, filed Mar. 11, 2009, titled Magnetic Connector, hereby incorporated by reference herein.

BACKGROUND OF THE INVENTION

Noninvasive physiological monitoring systems for measuring constituents of circulating blood have advanced from basic pulse oximeters to monitors capable of measuring abnormal and total hemoglobin among other parameters. A basic pulse oximeter capable of measuring blood oxygen saturation typically includes an optical sensor, a monitor for processing sensor signals and displaying results and a cable electrically interconnecting the sensor and the monitor. A pulse oximetry sensor typically has a red wavelength light emitting diode (LED), an infrared (IR) wavelength LED and a photodiode detector. The LEDs and detector are attached to a patient tissue site, such as a finger. The cable transmits drive signals from the monitor to the LEDs, and the LEDs respond to the drive signals to transmit light into the tissue site. The detector generates a signal responsive to the emitted light after attenuation by pulsatile blood flow within the tissue site. The cable transmits the detector signal to the monitor, which processes the signal to provide a numerical readout of oxygen saturation ($SpO_2$) and pulse rate. Advanced blood parameter monitors utilizing multiple LEDs that transmit a spectrum of wavelengths incorporate pulse oximetry and the capability of additional hemoglobin, perfusion and pulse measurements such as carboxyhemoglobin (HbCO), methemoglobin (HbMet), total hemoglobin (Hbt), total hematocrit (Hct), perfusion index (PI) and pulse variability index (PVI), as a few examples.

High fidelity pulse oximeters capable of reading through motion induced noise are disclosed in U.S. Pat. Nos. 6,770,028, 6,658,276, 6,157,850, 6,002,952 5,769,785, and 5,758,644, which are assigned to Masimo Corporation ("Masimo") and are incorporated by reference herein. Advanced physiological monitors and corresponding multiple wavelength optical sensors are described in at least U.S. patent application Ser. No. 11/367,013, filed Mar. 1, 2006, titled Multiple Wavelength Sensor Emitters and U.S. patent application Ser. No. 11/366,208, filed Mar. 1, 2006, titled Noninvasive Multi-Parameter Patient Monitor, assigned to Masimo Laboratories, Inc. and incorporated by reference herein. Noninvasive blood parameter monitors and corresponding multiple wavelength optical sensors, such as Rainbow™ adhesive and reusable sensors and RAD-57™ and Radical-7™ monitors are also available from Masimo.

SUMMARY OF THE INVENTION

Advanced physiological monitoring systems utilize a significant number of control and signal lines, creating a high pin density for sensor, cable and monitor connectors. This high pin density places a heavy demand on the connector mechanisms with respect to connect/disconnect ease, connection integrity, connector cost and life. A magnetic connector advantageously utilizes one or more of electromagnets, permanent magnets, magnetically permeable materials and air gaps to auto-align, attach, hold and release connectors for physiological monitoring applications.

One aspect of a magnetic connector is a receptacle and a plug. The receptacle has a wiring end, a receptacle contact end, a receptacle core, a coil and a receptacle contact set. The plug has a cable end, a plug contact end, a plug core and a plug contact set. An air gap is located in the receptacle core at the receptacle contact end. The coil, the core and the air gap form a magnetic circuit so that energizing the coil creates a magnetic field in the air gap. An anchor extends from plug core at the plug contact end so as to fit within the air gap. The receptacle contact set and the plug contact set electrically connect as the anchor inserts into the air gap.

In various embodiments, the receptacle core has an inner core and an outer core. The coil is wrapped around the inner core. The inner core and the outer core have concentric elongated circular receptacle edges that define the air gap. The plug core has an elongated circular plug edge that defines the anchor. The receptacle contact set has a socket block with contact apertures and contacts at least partially disposed within the contact apertures. The plug contact set has a pin block with pin apertures and pins at least partially disposed within the pin apertures. The pins insert into the contacts.

Additional embodiments include at least one permanent magnet disposed in either the anchor or the air gap or both. Power leads transmit current from a power source to the coil. A switch in series with one of the power leads is actuated either to block current in the power leads and de-energize the coil or to pass current in the power leads and energize the coil. An LED in series with one of the power leads illuminates according to the flow of current in the power leads so as to indicate if the coil is energized.

Another aspect of a magnetic connector involves interconnecting an optical sensor and a physiological monitor with a magnetic connector having a monitor receptacle and a cable plug. A receptacle core and a plug core are each constructed of magnetically permeable material. Receptacle contacts are housed within the receptacle core, and plug contacts are housed within the plug core. The receptacle core and the plug core are interconnected so as to electrically connect the receptacle contacts and the plug contacts. The receptacle core and the plug core are also magnetically coupled so as to maintain the interconnection. In an embodiment, a coil is wrapped around either the receptacle core or the plug core so as to form an electromagnet. An air gap is formed in the electromagnet core and an anchor is formed to extend from the other core. The anchor fits within the air gap. Current to the coil is switched on or off so that the electromagnet assists in locking the anchor within the air gap or releasing the anchor from the air gap.

In various embodiments, at least one permanent magnet is embedded within one of the cores. If a permanent magnet is embedded within or near the anchor or near the air gap, then the permanent magnet locks the anchor within the air gap when the coil is de-energized. When the coil is energized, it creates an opposing field to the permanent magnet within the air gap so as to release the anchor. This permanent-magnet-based magnetic coupling holds the receptacle and plug together when the coil is de-energized, but allows the receptacle and plug to be easily disconnected by briefly energizing the coil.

A further aspect of a magnetic connector is first and second magnetic elements having first and second contact sets. The first contact set is housed proximate the first magnetic element, and the second contact set is housed proximate the second magnetic element. At least one of the magnetic elements is responsive to a current input so as to alter a magnetic coupling between the magnetic elements. The magnetic coupling assists in making or breaking an electrical connection between the first and second contact sets. In an embodiment, the first magnetic element comprises a core of magnetically permeable material, a conductive coil having "N" turns disposed around at least a portion of the core, coil leads in communications with a current source and an air gap defined within the core. The current source has "I" amps energizing the coil so as to generate a electromagnetic field within the air gap proportional to N times I. In an embodiment, the second magnetic element comprises an anchor of magnetically permeable material sized to closely fit within the air gap. The contact sets make an electrical connection as the anchor is manually inserted into the air gap and break an electrical connection as the anchor is manually withdrawn from the air gap. The anchor locks within the air gap in response to a magnetic field within the air gap so as to maintain an electrical connection between the contact sets.

In various other embodiments, a switch in series with the coil controls whether the coil is energized, and an LED in series with the switch indicates whether the coil is energized. A permanent magnet is incorporated within the first magnetic element near the air gap and/or within the second magnetic element in or near the anchor. The permanent magnet has poles oriented so that its magnetic field opposes the air gap field.

In yet another embodiment, a magnetic connector has a plug means and a corresponding receptacle means for interconnecting a sensor and a corresponding monitor. The magnetic connector also has a socket means and a corresponding pin means housed within the plug means and the receptacle means for making and breaking electrical communications between sensor conductors and monitor conductors as the plug is inserted into and removed from the receptacle, respectively. Further, the magnetic connector has a pair of mating magnetic element means housed within the plug means and the receptacle means for assisting in at least one of the making and breaking of electrical communications between the socket means and the pin means. In an embodiment, the mating magnetic element means comprises an electromagnet means for generating a magnetic field within an air gap and an anchor means for locking within and releasing from the air gap according to power provided to the electromagnet means. Various other embodiments include a permanent magnet means for opposing the air gap magnetic field disposed proximate at least one of the air gap and the anchor means, a switch means for manually controlling the air gap magnetic field so as to secure or release the anchor means within the air gap and/or an indicator means for visually identifying the state of the air gap magnetic field.

DESCRIPTION OF THE DRAWINGS

FIGS. 6A-E' are cross sectional exploded, disconnected, connected and detailed views of receptacle and plug core assemblies;

DETAILED DESCRIPTION OF THE PREFERRED EMBODIMENTS

Figure 1:
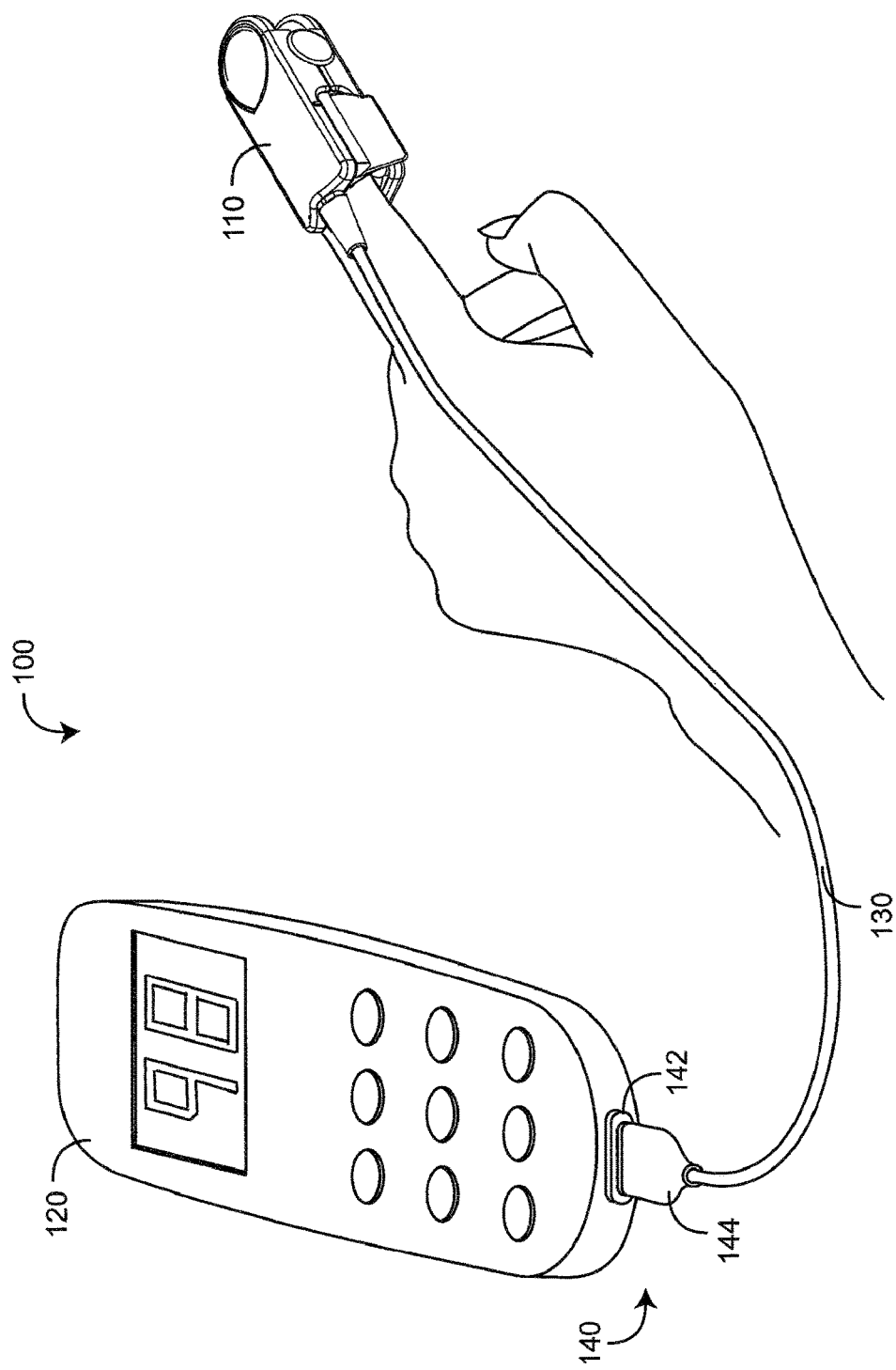
FIG. 1 is a perspective view of a physiological monitoring system having a magnetic connector.

FIG. 1 illustrates a physiological monitoring system 100 having a sensor 110, a monitor 120, a cable 130 interconnecting the sensor 110 and the monitor 120, and a magnetic connector 140. The magnetic connector 140 has a receptacle 142 mounted in the monitor 120 and a plug 144 terminating the cable 130. Advantageously, the magnetic connector 140 utilizes magnetic fields generated by combinations of electromagnets, permanent magnets, magnetically permeable materials and air gaps to auto-align, attach, hold and release the receptacle 142 and plug 144. In this manner, a relatively small connector having the high contact density needed for advanced physiological monitoring applications can be made to have ease of use, durability and low cost characteristics. These characteristics are particularly important for handheld monitoring applications. Various combinations of sensor 110, monitor 120, cable 130 and magnetic connector 140 are described with respect to FIGS. 2A-D, below.

Figure 2A:
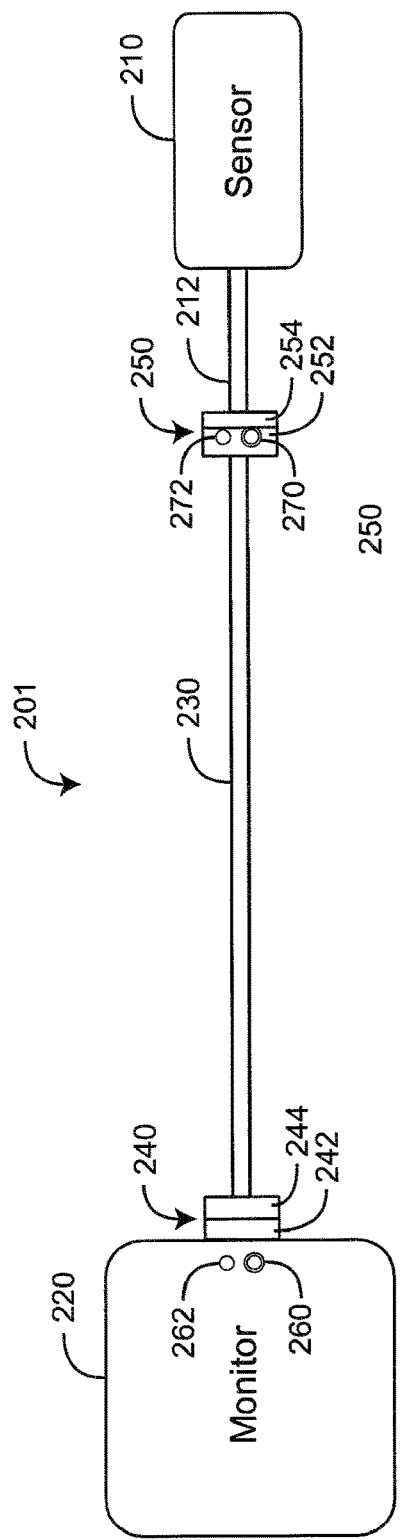
FIGS. 2A-D are illustrations of different magnetic connector configurations for connecting a sensor and a monitor.
Figure 2B:
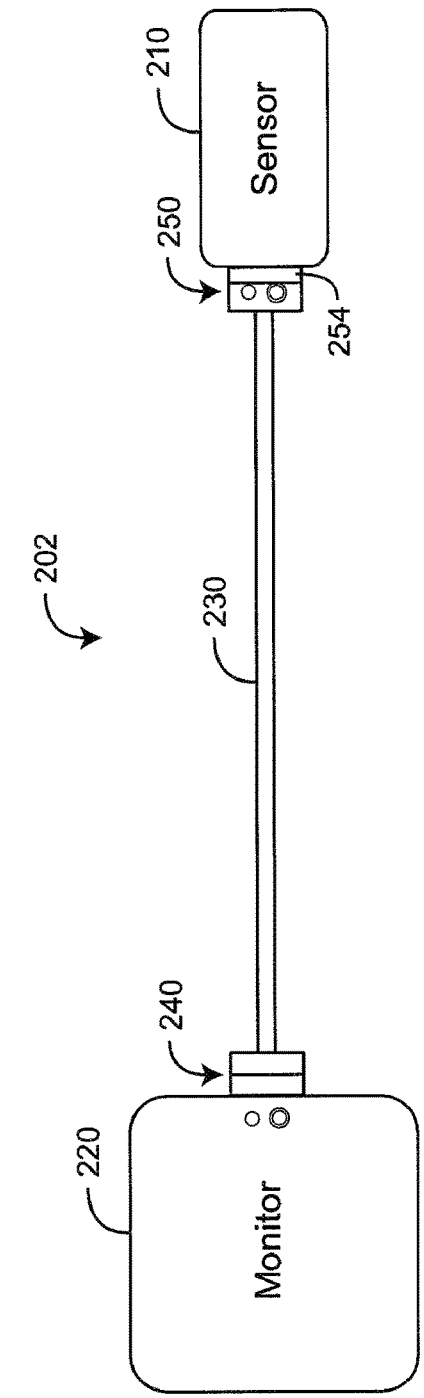
Figure 2C:
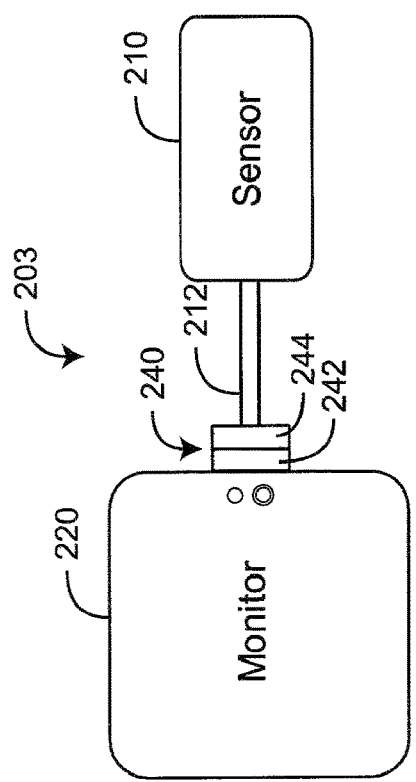
Figure 2D:
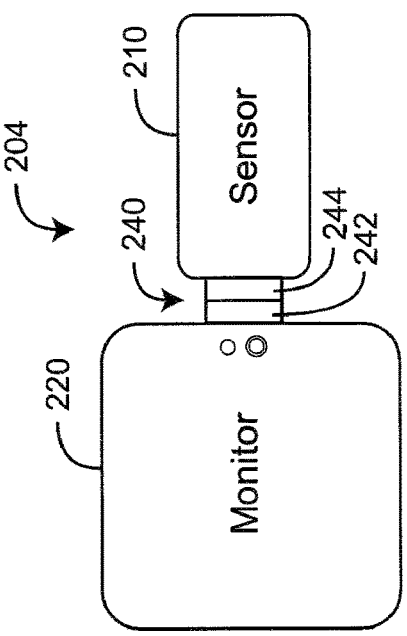

FIGS. 2A-D illustrate different configurations of one or more magnetic connectors 240, 250 utilized to connect a sensor 210 and a monitor 220. FIGS. 2A-B illustrate dual magnetic connector configurations and FIGS. 2C-D illustrate single magnetic connector configurations. As shown in FIG. 2A, in a first configuration, a sensor 210 is connected to a monitor 220 via a patient cable 230 and a sensor cable 212. The patient cable 230 is a standalone component and the sensor cable 212 is integral to the sensor 210. A first magnetic connector 240 is disposed proximate the monitor 220 for connecting the patient cable 230 to the monitor 220. A second magnetic connector 250 is disposed between the patient cable 230 and the sensor cable 212 for connecting the patient cable 230 to the sensor 210.

In particular, the first magnetic connector 240 has a receptacle 242 mounted to the monitor 220 and a plug 244 mounted to one end of the patient cable 230. A magnetic field provides at least some force for assisting a person to join and/or disjoin the receptacle 242 and plug 244 so as to electrically connect and/or disconnect patient cable 230 conductors and monitor 220 conductors. The monitor 220 has a button 260 that is actuated so as to energize/deenergize the magnetic field in the receptacle 242. The monitor 220 also has an indicator light 262 that signals the magnetic field status as on or off.

Similarly, the second magnetic connector 250 has a receptacle 252 mounted to one end of the patient cable 230 and a plug 254 mounted to the end of the sensor cable 212.

Likewise, a magnetic field provides at least some force for assisting a person to join and/or disjoin the receptacle 252 and plug 254 so as to electrically connect and/or disconnect patient cable 230 conductors and sensor cable 212 conductors. Also, the patient cable receptacle 252 has a button 270 so as to energize/de-energize the magnetic field in the receptacle 252 and an indicator light 272 that signals the magnetic field status as on or off. A magnetic connector embodiment including a receptacle and a plug are described with respect to FIGS. 5-11, below.

As shown in FIG. 2B, in a second configuration, a sensor 210 is connected to a monitor 220 via a patient cable 230. A first magnetic connector 240 is disposed proximate the monitor 220 and a second magnetic connector 250 is disposed proximate the sensor 210 for interconnecting the sensor 210 and the monitor 220 via the sensor cable 230. The first magnetic connector 240 is as described with respect to FIG. 2A, above. The second magnetic connector 250 is as described with respect to FIG. 2A, above, except that the plug portion 254 is disposed proximate the sensor 210.

As shown in FIG. 2C, in a third configuration, a sensor 210 is connected to a monitor 220 via a sensor cable 212. A single magnetic connector 240 is disposed proximate the monitor 220 for connecting the monitor 220 to the sensor 210 via the sensor cable 212. The magnetic connector 240 has a receptacle 242 mounted to the monitor 220 and a plug 244 mounted to the end of the sensor cable 212 for interconnecting the sensor 210 and the monitor 220. Otherwise, the magnetic connector 240 is as described with respect to FIG. 2A, above.

As shown in FIG. 2D, in a fourth configuration, a sensor 210 is connected directly to a monitor 220. A single magnetic connector 240 is disposed between the monitor 220 and sensor 210. In particular, the magnetic connector 240 has a receptacle 242 disposed proximate the monitor 220 and a plug 244 disposed proximate the sensor 210. Otherwise, the magnetic connector 240 is as described with respect to FIG. 2A, above.

As described with respect to FIGS. 2A-D, a monitor 220 may be, as examples, any of a multi-parameter patient monitoring system (MPMS), a plug-in to a MPMS, a stand-alone monitor, a handheld monitor, a handheld monitor docked to a docking station, a personal monitoring device or any physiological parameter calculating device that processes one or more sensor signals to derive a physiological measurement. As described above, a sensor 210 may be a reusable, resposable or disposable sensor; an optical transmission or reflection sensor; a blood pressure sensor; a piezo-electric or other acoustic sensor; an assembly of EKG or EEG electrodes; or any non-invasive or invasive device for providing physiological signals to a monitoring or calculating device.

Figure 3:
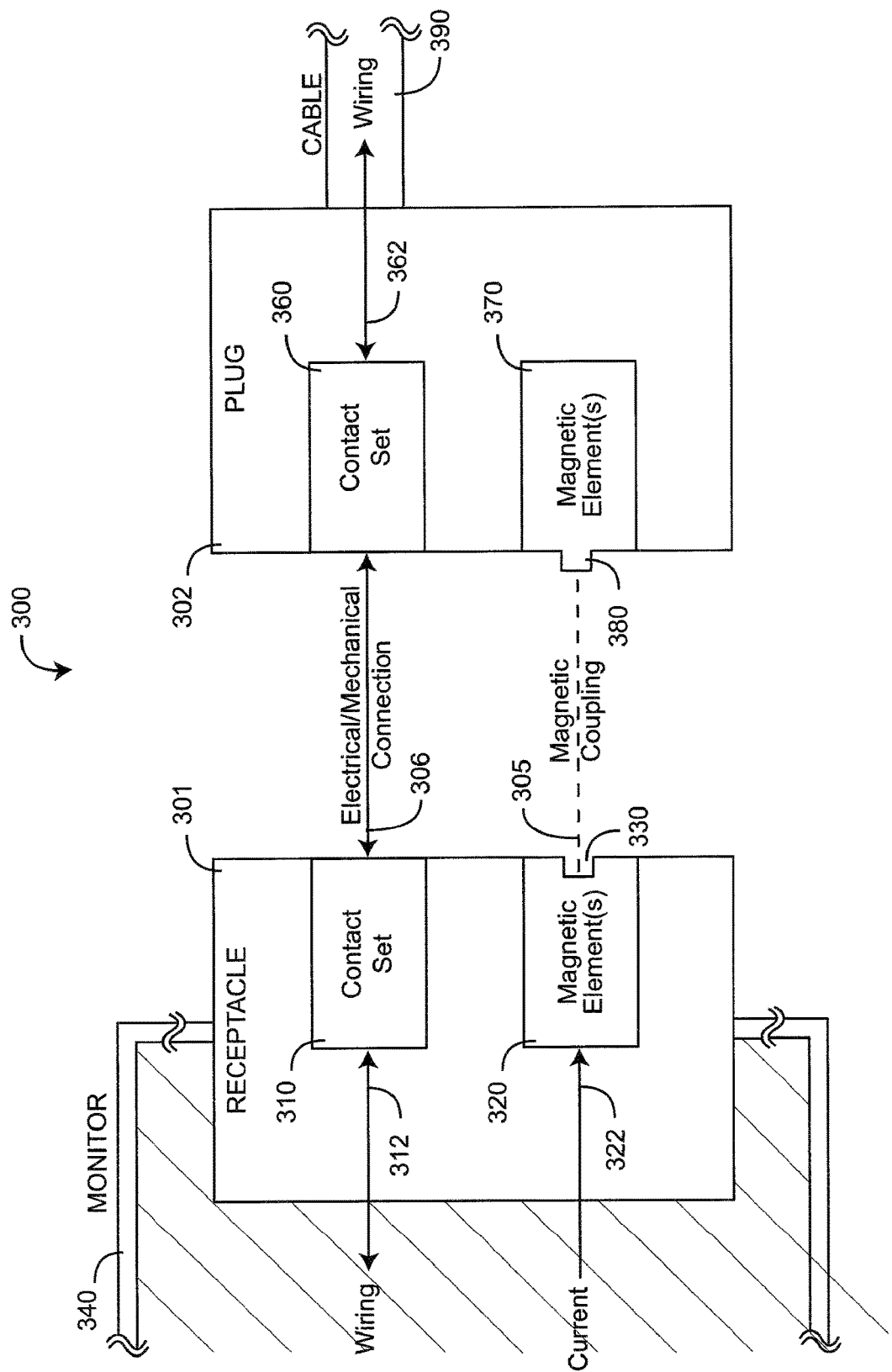
FIG. 3 is a general block diagram of a magnetic connector.

FIG. 3 generally illustrates a magnetic connector 300 having a receptacle 301 and a plug 302. The receptacle 301 has a contact set 310 and magnetic element(s) 320. The plug 302 has a contact set 360 and magnetic element(s) 370. The magnetic element pair 320, 370 provides a magnetic coupling 305 between receptacle 301 and plug 302. This magnetic coupling assists a user in making or breaking the electrical/mechanical connection between the contact sets 310, 360, making or breaking continuity between receptacle wiring 312 and plug wiring 362. In a particularly advantageous embodiment, the receptacle magnetic element(s) 320 incorporate an electromagnet. When energized by a current source 322, the electromagnet generates a magnetic field within an air gap 330 so as to attract or repel a corresponding anchor 380 that closely fits within the air gap 330. In various embodiments, the magnetic elements 320, 370 may include one or more of electromagnets, permanent magnets, materials with high magnetic permeability, air gaps and anchors. In various embodiments, the receptacle or plug may be integrated with a monitor, such as mounted to a monitor chassis, or attached to a sensor cable or patient cable, for example.

Figure 4A:
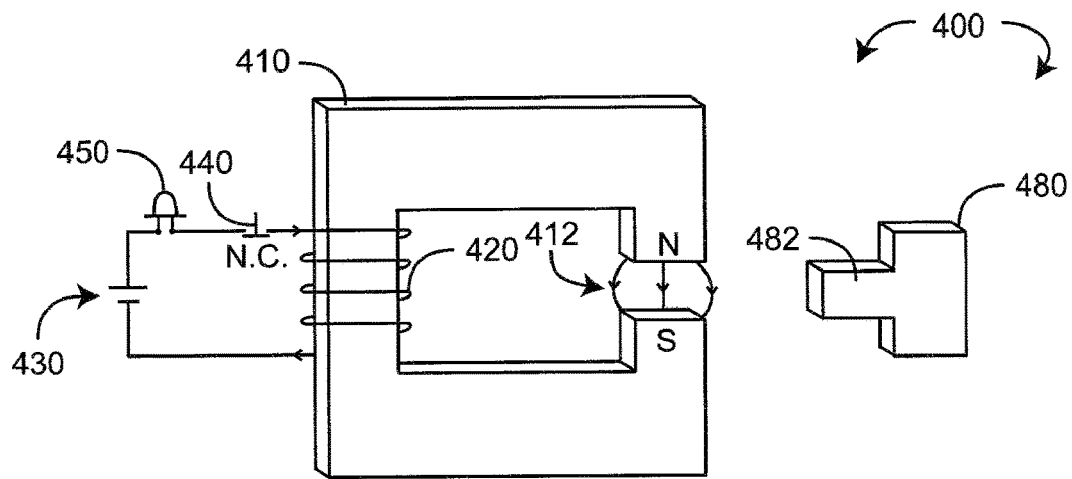
FIGS. 4A-C are illustrations of various magnetic coupling mechanisms incorporated within a magnetic connector.
Figure 4B:
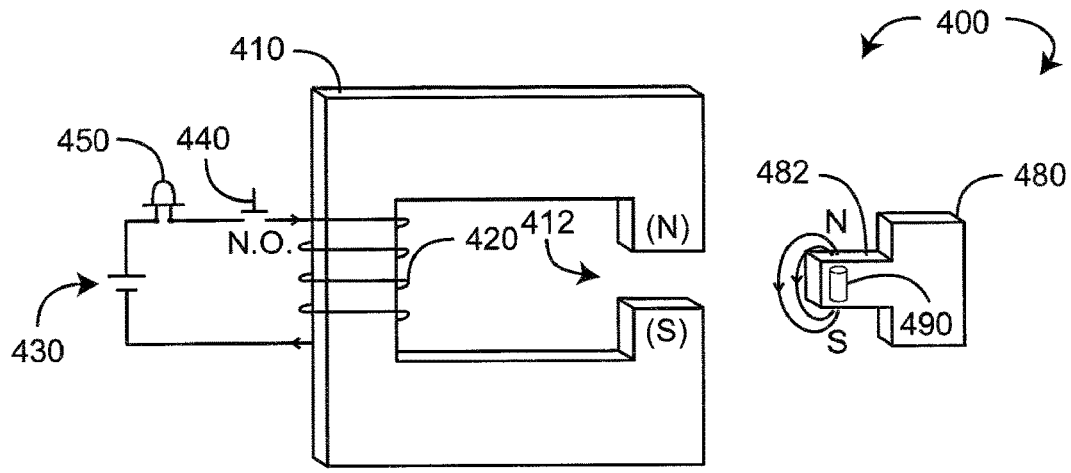
Figure 4C:
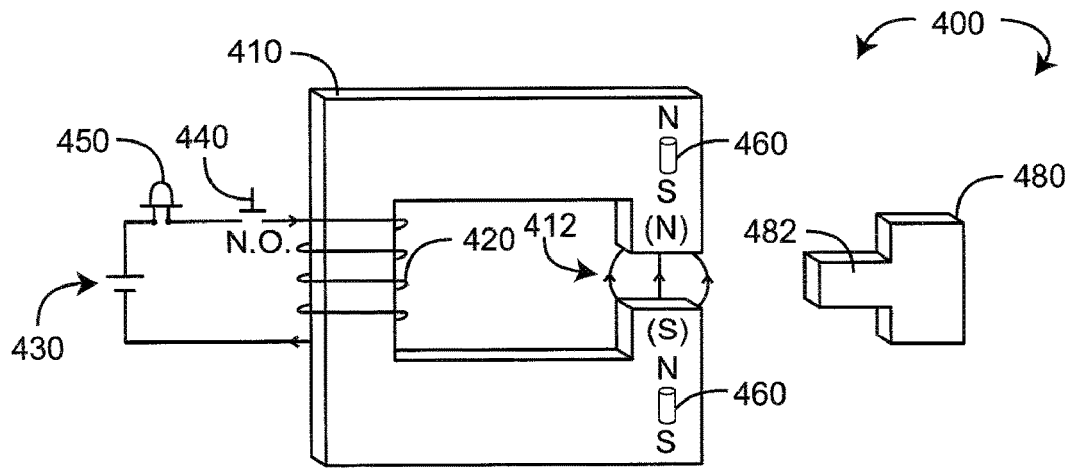

FIGS. 4A-C generally illustrate various magnetic coupling 305 (FIG. 3) embodiments between the receptacle and plug of a magnetic connector, such as generally described above with respect to FIG. 3. These embodiments include a receptacle core 410 defining an air gap 412 and a corresponding plug core 480 defining an anchor 482. An electromagnet is formed from the receptacle core 410, a coil 420, a DC current source 430, a switch 440 and an indicator 450. When the switch 440 is closed, the coil 420 is energized, the indicator 450 is on and the electromagnet generates a magnetic field within the air gap 412. When the switch 440 is opened, the coil 420 is de-energized, the indicator 450 is off and the air gap magnetic field is extinguished. The receptacle core 410 and plug core 480 are constructed of materials having a high magnetic permeability. A substantial magnetic field is created in the air gap 412 having north "N" and south "S" polarities as shown. The receptacle core 410 and plug core 480 can be any of a variety of shapes and sizes. For example, the embodiment described below with respect to FIGS. 5-11 utilizes a receptacle core that defines an elongated, circular air gap and a plug core that defines a corresponding elongated, circular anchor.

As shown in FIG. 4A, in a first embodiment, the plug core 480 or at least the anchor 482 is a soft iron material and the switch 440 is normally closed (N.C.). Accordingly, D.C. current normally flows in the coil 420 and a magnetic field is maintained in the air gap 412. As such, the anchor 482 is attracted to and held within the air gap 412, locking the corresponding plug (not shown) to the corresponding receptacle (not shown). The switch 440 is actuated to interrupt the D.C. current, which releases the anchor 482 from the air gap 412 and allows the plug to be pulled from the receptacle.

As shown in FIG. 4B, in a second embodiment, the plug core 480 is a permanent magnet or is a material with a high magnetic permeability embedded with one or more permanent magnets 490. The permanent magnet field attracts the anchor 482 to the air gap 412, so as to lock a corresponding plug to a corresponding receptacle. The switch 440 is normally open (N.O.). Accordingly, actuating the switch 440 pulses the D.C. current to the coil 420, temporarily creating an opposing field (N), (S) within the air gap 412. This releases the anchor 482 from the air gap 412 and allows the plug to be pulled from the receptacle.

As shown in FIG. 4C, in a third embodiment, the plug core 480 is a soft iron material. One or more permanent magnets 460 are embedded within the receptacle core 410. The permanent magnet field attracts the anchor 482 to the air gap 412, so as to lock a corresponding plug to a corresponding receptacle. The switch 440 is normally open (N.O.). Accordingly, actuating the switch 440 pulses the D.C. current to the coil 420, temporarily creating an opposing field (N), (S) within the air gap 412. This releases the anchor 482 from the air gap 412 and allows the plug to be pulled from the receptacle.

FIGS. 5A-F illustrate a magnetic connector embodiment 500 having a receptacle 501 and a plug 502. The receptacle 501 is mountable to a device, such as a physiological monitor. The plug 502 is attachable to a sensor cable or a patient cable. The receptacle 501 has a core 700, 800 (FIGS. 5E-F) that defines an elongated circular air gap 510. The plug 502 has a core 1000 (FIGS. 5E-F) that defines an elongated circular anchor 550, which inserts within the air gap 510. The receptacle core 700, 800 and corresponding coil 600 (FIGS. 5E-F) form an electromagnet that, when energized, generates a magnetic field within the air gap 510. Depending on the configuration, the electromagnetic field holds or releases the anchor 550 from the air gap 510 so as to lock or unlock the connection between the receptacle 501 and plug 502.

Figure 5A:
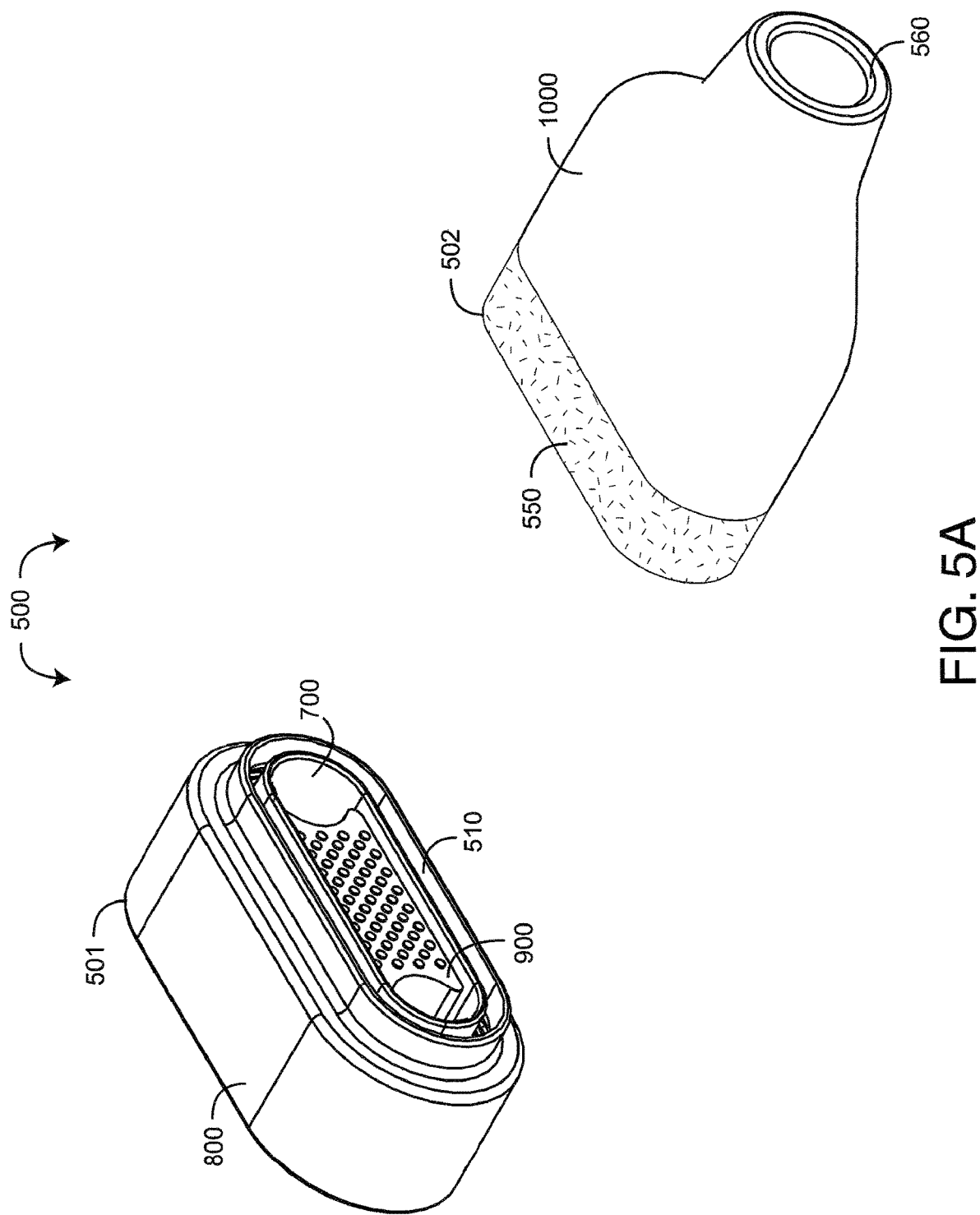
FIGS. 5A-F are front and back, perspective and exploded, connected and disconnected views of a magnetic connector receptacle and plug.
Figure 5B:
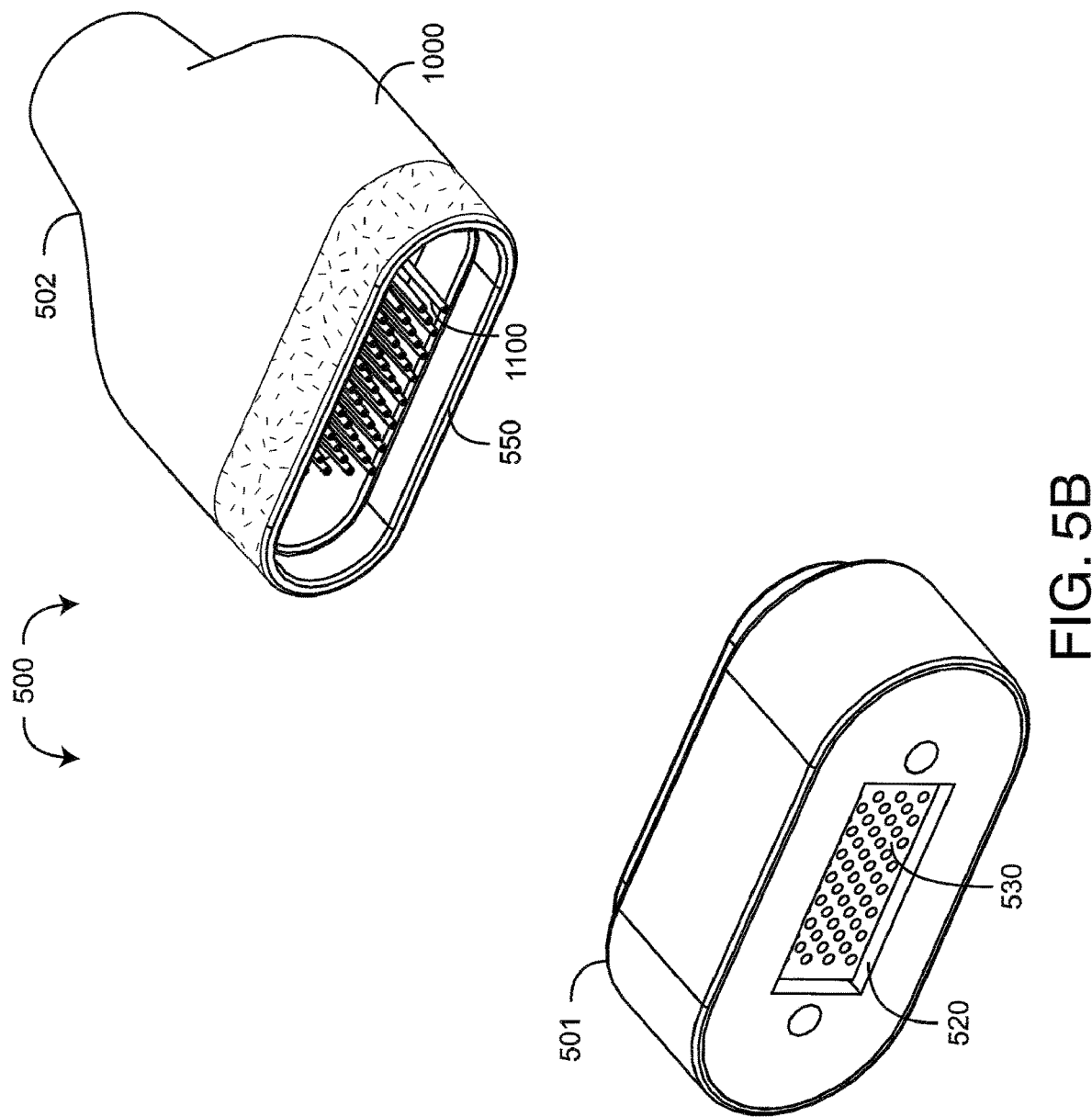
Figure 5D:
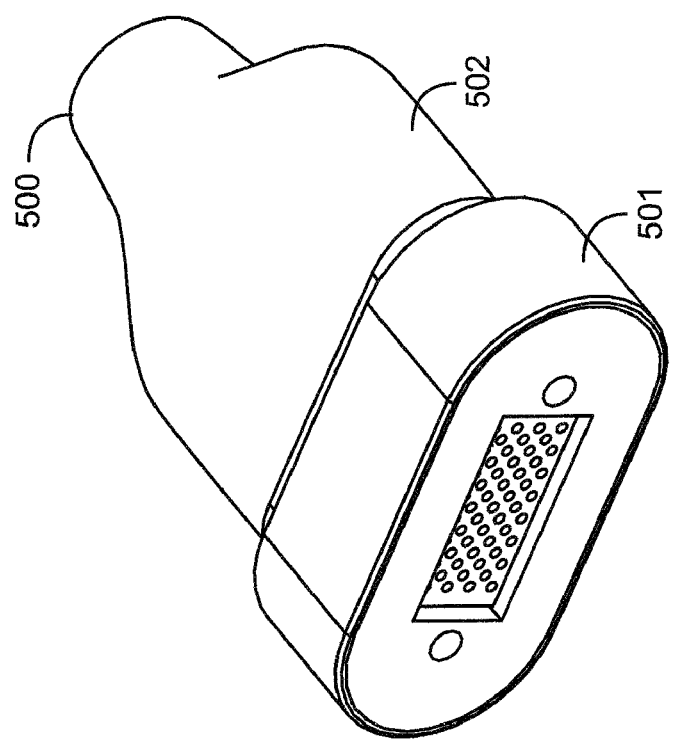
Figure 5C:
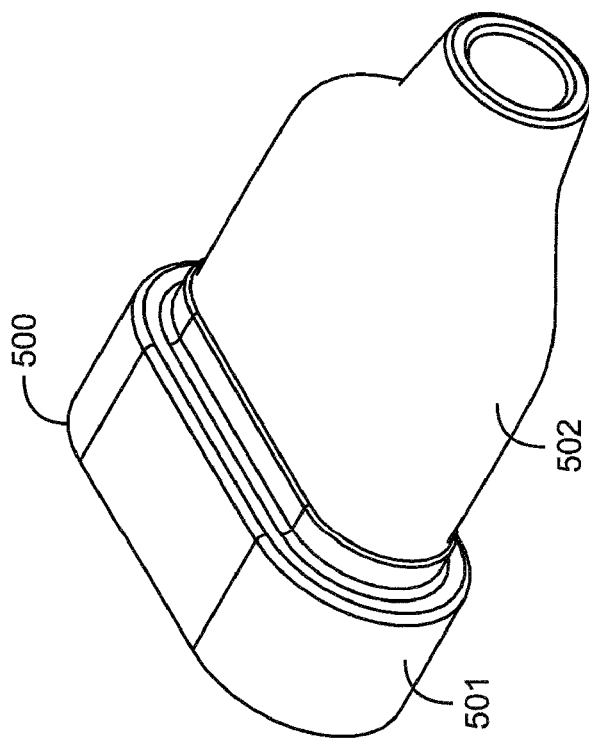

Also shown in FIGS. 5A-F, the receptacle 501 has a receptacle contact set 900 and the plug 502 has a plug contact set 1100. When the receptacle 501 and plug 502 are connected, the plug contact set 1100 inserts into the receptacle contact set 900, electrically coupling the receptacle 501 and socket 502. This electrical coupling provides an electrical path between cable conductors attached to the plug 502 at a cable end 560 (FIG. 5A) and wires attached to the receptacle 501 at a device end 530 (FIG. 5B).

Figure 5E:
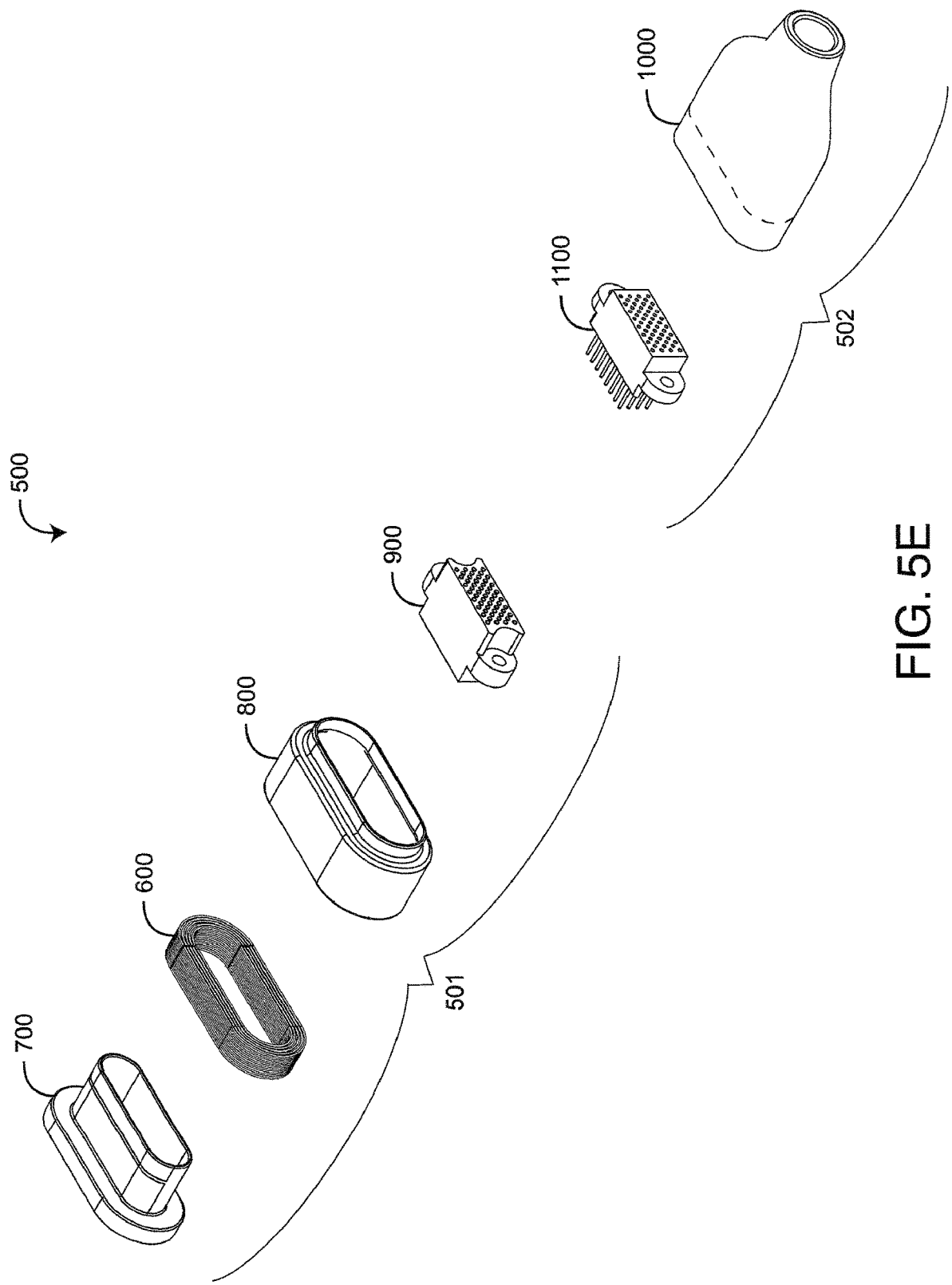
Figure 5F:
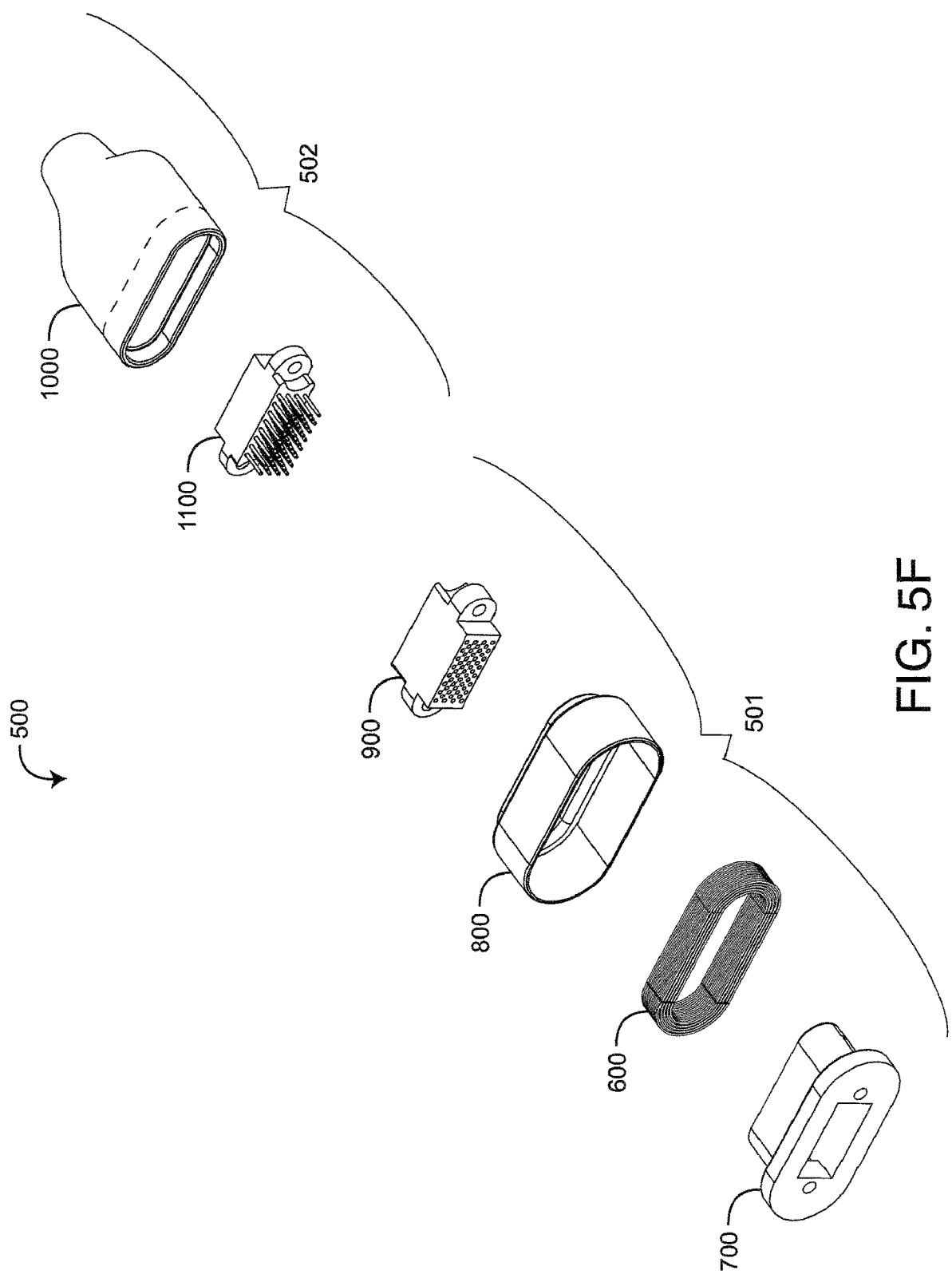

As shown in FIGS. 5E-F, the receptacle 501 has a coil 600, an inner core 700, an outer core 800 and a contact set 900. The receptacle core 700, 800 forms a receptacle housing. In particular, the coil 600 is wound around the inner core 700 and enclosed by the outer core 800. The contact set 900 is mounted inside the inner core 700. The plug 502 has a core 1000 and a contact set 1100. The plug core 1000 forms a plug housing, and the contact set 1100 is mounted inside the plug core 1000.

Figure 6E:
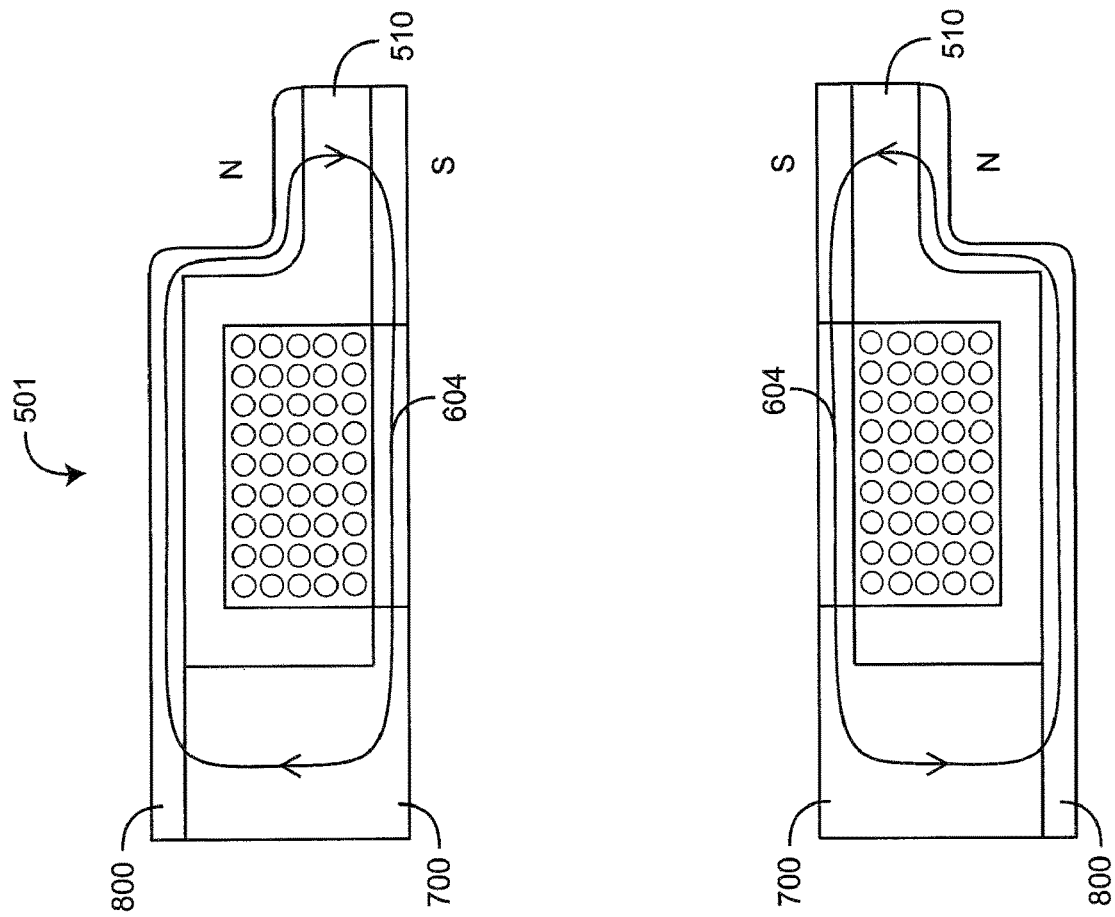
Figure 6D:
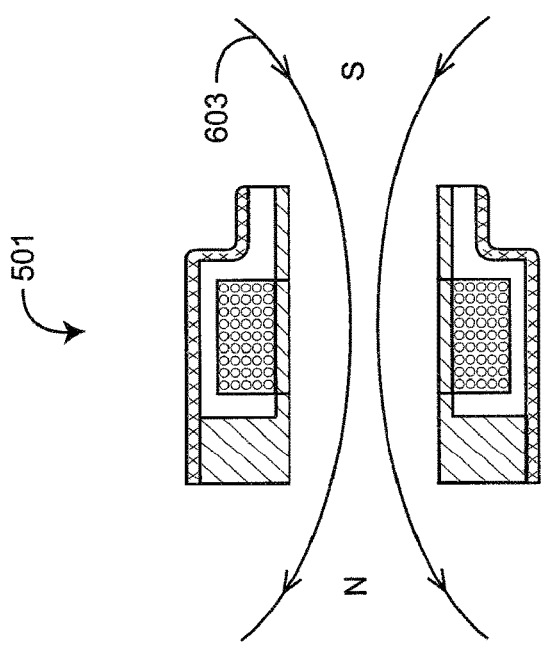
Figure 7B:
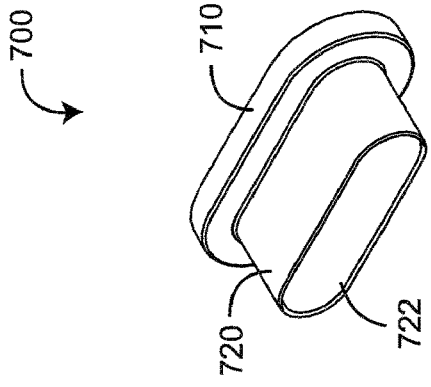
FIGS. 7A-D are top, perspective, front and side views, respectively, of a receptacle inner core.
Figure 7D:
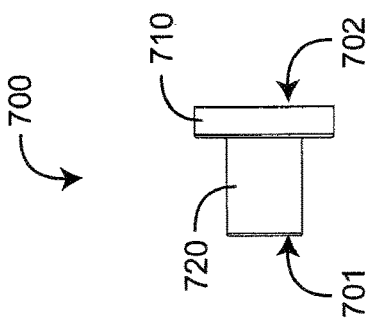
Figure 7A:
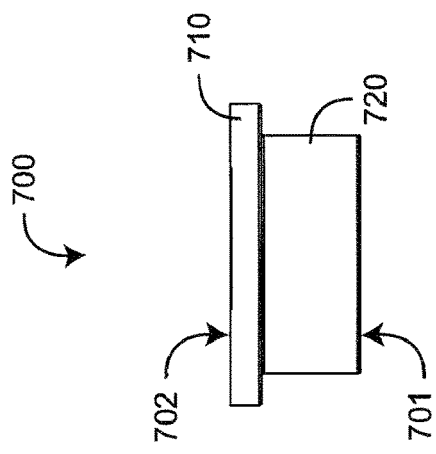
Figure 7C:
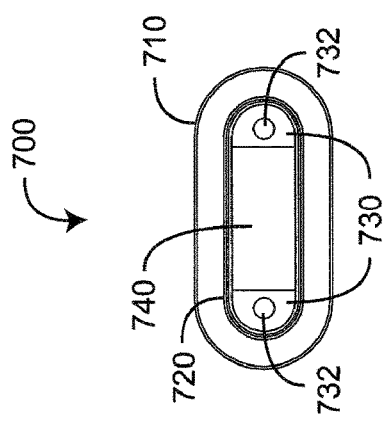
Figure 8B:
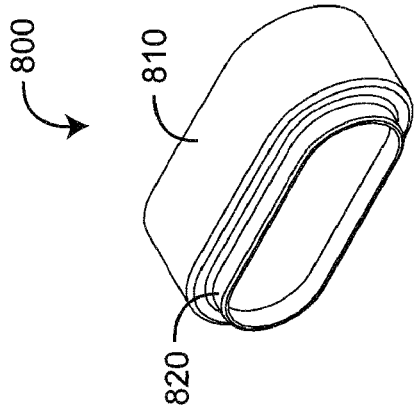
FIGS. 8A-D are top, perspective, front and side views, respectively, of a receptacle outer core.
Figure 8D:
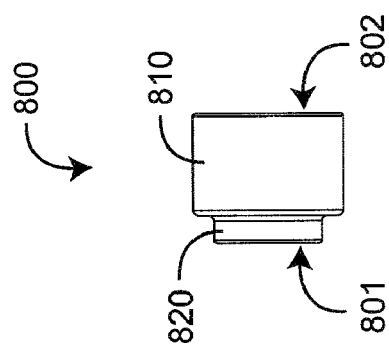
Figure 8A:
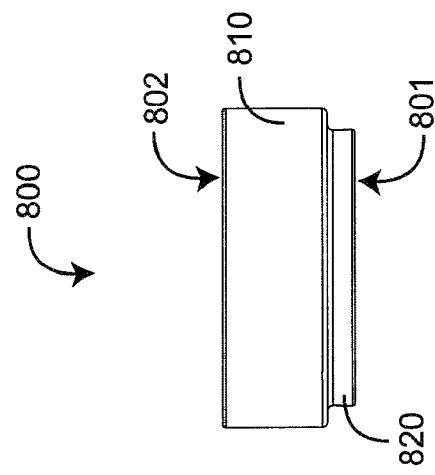
Figure 8C:
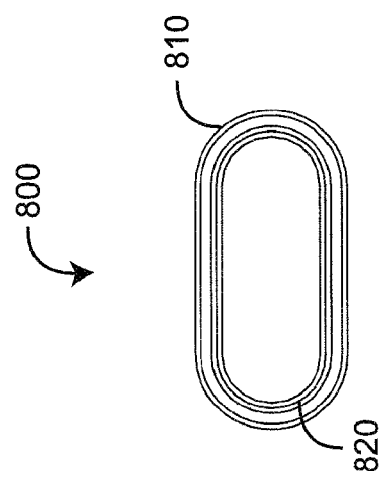
Figure 9B:
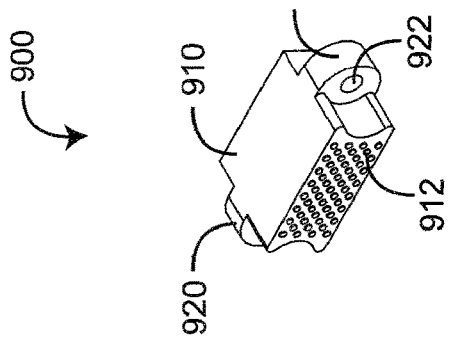
FIGS. 9A-D are top, perspective, front and side views, respectively, of a receptacle contact set.
Figure 9D:
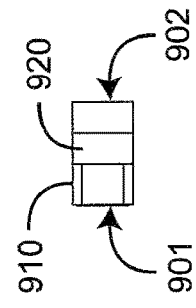
Figure 9A:
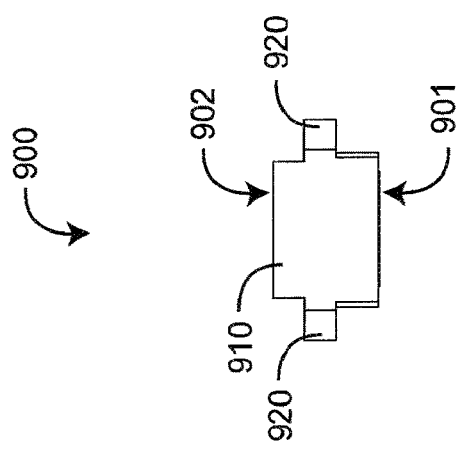
Figure 9C:
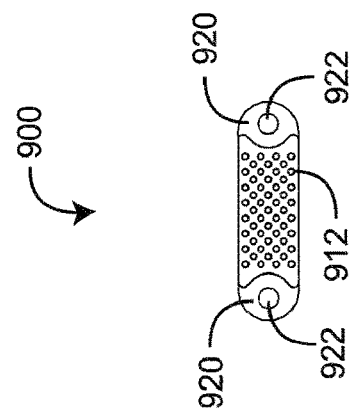
Figure 10A:
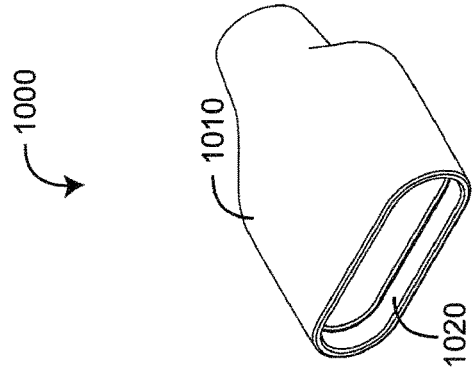
FIGS. 10A-D are top, perspective, front and side views, respectively, of a plug core.
Figure 10B:
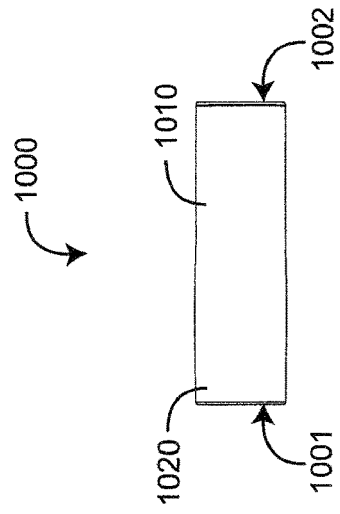
Figure 10C:
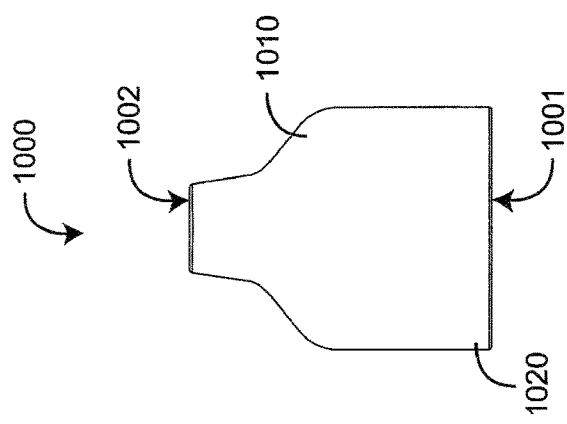
Figure 10D:
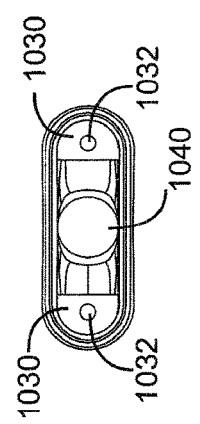
Figures 11A, 11B, 11C, 11D:
FIGS. 11A-D are top, perspective, front and side views, respectively, of plug contact set.

FIGS. 6A-E are cross-sections of the receptacle core 700, 800 and plug core 1000. As shown in FIGS. 6A-C, the coil 600 is wound around the receptacle inner core 700 and enclosed by the outer core 800. Thus configured, the front edges of the receptacle core 700, 800 form an air gap 510. Likewise, the front edge of the plug core 1000 forms an anchor 550 that inserts (FIG. 6C) into the air gap 510. As shown in FIG. 6D, if DC current flows in the top-half of the coil in a direction into the page and in the bottom-half of the coil in a direction out of the page, then the magnetic field 603 produced by the coil has a north pole, N, at the left and a south pole, S, at the right (right-hand rule). As shown in FIG. 6E, the magnetic flux 604 in the receptacle core resulting from the magnetic field 603 is mostly confined within the walls of the receptacle core 700, 800, and results in a magnetic field in the air gap 510 as shown. As a result, the magnetic field in the air gap 510 has a north pole at the outer core portion and a south pole at the inner core portion. Thus, a "slice" of the receptacle core 700, 800 and corresponding air gap 510 are analogous to the core and air gap described with respect to FIGS. 4A-C, above. Likewise, a "slice" of the plug core 1000 and plug anchor 550 are analogous to the plug core and anchor described with respect to FIGS. 4A-C, above.

FIGS. 7-11 illustrate further details of the receptacle inner core 700, outer core 800, receptacle contact set 900, plug core 1000 and plug contact set 1100. As shown in FIGS. 7A-D, the receptacle inner core 700 mounts the receptacle contact set 900 (FIGS. 9A-D), supports the coil 600 (FIGS. 5E-F), and defines a portion of the receptacle core air gap 510 (FIG. 5A). The inner core 700 has a planar base 710 defining a back side 702 and a tubular coil support 720 extending from the base 710 and defining a front side 701. Both the base 710 and the coil support 720 have an elongated, circular cross-section. Inside the coil support 720 is a bracket 730 and corresponding bracket holes 732 for mounting the receptacle contact set 900 (FIGS. 9A-D). A wiring aperture 740 provides wiring access to the contact set 900 from the back side 702. An elongated circular edge 722 defines a portion of the air gap 510 (FIG. 5A) at the front side 701. In an embodiment (not shown), the base 710 provides chassis mounts for attaching the receptacle 501 (FIGS. 5A-B) to a monitor.

As shown in FIGS. 8A-D, the receptacle outer core 800 houses the coil, inner core and contact set and defines a portion of the receptacle core air gap 510 (FIG. 5A). The outer core 800 has a tubular housing 810 defining a back side 802 and a tubular edge 820 extending from the housing 810 and defining a front side 801. Both the housing 810 and the edge 820 have elongated circular cross-sections, with the edge 820 cross-section having a smaller circumference than the housing 810 cross-section. The edge 820 also defines a portion of the air gap 510 (FIG. 5A).

As shown in FIGS. 9A-D, the receptacle contact set 900 has a front side 901, a back side 902, a socket block 910 and corresponding contacts (not visible). The socket block 910 has a generally rectangular cross-sectioned body 910 and generally circular mounting ears 920 extending from the block sides. The ears have ear holes 922 that accept fasteners. The socket block 910 also has several rows of apertures 912 that extend from the front side 901 to the back side 902. Conductive contacts (not visible) are disposed within the apertures 912 and are configured to mate with corresponding plug pins 1130 (FIGS. 11A-D), described below. The receptacle contact set 900 mounts within the inner core 700 (FIGS. 7A-D) so that the mounting ears 920 rest on the core bracket 730 (FIGS. 7A-D). The contact set 900 is attached to the inner core 700 (FIGS. 7A-D) with fasteners disposed through the ear holes 922 and mounting holes 732 (FIGS. 7A-D).

As shown in FIGS. 10A-D, the plug core 1000 mounts the plug contact set 1100 (FIGS. 11A-D) and defines an anchor 550 (FIG. 5B) that releasably locks within the receptacle air gap 510 (FIG. 5A). The plug core 1000 has a tubular housing 1010 defining a back side 1002 and a tubular edge 1020 extending from the housing 1010 and defining a front side 1001. The edge 1020 has an elongated, circular cross-section. The housing 1010 has an elongated, circular cross-section near the front side 1001 and a circular cross-section near the back side that accommodates a cable (not shown). Inside the housing 1010 is a bracket 1030 and corresponding bracket holes 1032 for mounting the plug contact set 1100 (FIGS. 11A-D). A cable aperture 1040 provides cable entry for wiring access to the plug contact set 1100 (FIGS. 11A-D) via the back side 1002. The elongated circular edge 1020 defines the anchor 550 (FIG. 5B) at the front side 1001.

As shown in FIGS. 11A-D, the plug contact set 1100 has a front side 1101, a back side 1102, a pin block 1110 and corresponding pins 1130. The pin block 1110 has a generally rectangular cross-sectioned body having generally circular mounting ears 1120 extending from the block sides. The ears 1120 have ear holes 1122 that accept fasteners. The pin block 1110 also has several rows of apertures 1112 that extend from the front side 1101 to the back side 1102. Conductive pins 1130 are disposed within the apertures 1112 and are configured to mate with corresponding receptacle contacts, described above. The contact set 1100 mounts within the plug core 1000 (FIGS. 10A-D) so that the mounting ears 1120 rest on the core bracket 1030 (FIGS. 10A-D). The contact set 1100 is attached to the receptacle core 1000 (FIGS. 10A-D) with fasteners disposed through the ear holes 1122 and mounting holes 1032 (FIGS. 10A-D).

A magnetic connector has been disclosed in detail in connection with various embodiments. These embodiments are disclosed by way of examples only and are not to limit the scope of the claims that follow. One of ordinary skill in art will appreciate many variations and modifications.

What is claimed is:

1. A magnetic connector for a low voltage data communications cable, the magnetic connector comprising:
    a contact set configured to couple with a corresponding contact set of a corresponding connector;
    an energizeable magnetic circuit configured to align and hold the contact set in place with the corresponding contact set of the corresponding connector, the energizeable magnetic circuit configured to energize and deenergize to cause the contact set to attract and release the corresponding connector.

2. The magnetic connector of claim 1, wherein the magnetic connector is comprised as part of a physiological sensor.

3. The magnetic connector of claim 1, wherein the magnetic connector connects to a physiological monitoring system.

4. The magnetic connector of claim 1, wherein the energizeable magnetic circuit comprises one or more of electromagnets or permanent magnets.

5. The magnetic connector of claim 1, further comprising a button configured to energize and deenergize the magnetic circuit.

6. The magnetic connector of claim 1, further comprising an air gap.

7. The magnetic connector of claim 6, wherein the energizeable magnetic circuit generates a magnetic field only within the air gap.

* * * * *